(12) United States Patent
Hopper et al.

(10) Patent No.: US 7,335,654 B2
(45) Date of Patent: Feb. 26, 2008

(54) PHOSPHODIESTERASE 4 INHIBITORS

(75) Inventors: Allen T. Hopper, Glen Rock, NJ (US); Ruiping Liu, Huntington, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 411 days.

(21) Appl. No.: 10/636,996

(22) Filed: Aug. 8, 2003

(65) Prior Publication Data

US 2004/0102460 A1 May 27, 2004

Related U.S. Application Data

(60) Provisional application No. 60/401,764, filed on Aug. 8, 2002.

(51) Int. Cl.
  *C07D 473/40* (2006.01)
  *A61K 31/52* (2006.01)
  *A61K 31/522* (2006.01)
  *A61P 25/28* (2006.01)
  *A61P 25/16* (2006.01)

(52) U.S. Cl. .................. 514/234.2; 544/264; 544/265; 544/277; 544/118; 544/326; 544/328; 514/263.2; 514/263.21; 514/263.22; 514/263.23; 514/263.1; 514/263.3; 514/263.4

(58) Field of Classification Search ...................... None
See application file for complete search history.

(56) References Cited

U.S. PATENT DOCUMENTS

| | | | |
|---|---|---|---|
| 3,917,583 A | 11/1975 | Meyer et al. | |
| 3,919,192 A | 11/1975 | Meyer et al. | |
| 5,013,829 A | 5/1991 | Nair et al. | |
| 5,073,559 A * | 12/1991 | Coates | 514/263.3 |
| 5,525,606 A * | 6/1996 | Moschel et al. | 514/263.37 |
| 5,744,473 A | 4/1998 | Chasin et al. | |
| 5,814,651 A | 9/1998 | Duplantier et al. | |
| 5,864,037 A | 1/1999 | Chasin et al. | |
| 5,935,978 A | 8/1999 | Fenton et al. | |
| 5,939,422 A | 8/1999 | Cavalla et al. | |
| 6,037,470 A | 3/2000 | Cavalla et al. | |
| 6,040,447 A | 3/2000 | Cavalla et al. | |
| 6,057,445 A | 5/2000 | Cavalla et al. | |
| 6,211,367 B1 | 4/2001 | Cavalla et al. | |
| 6,228,859 B1 | 5/2001 | Cavalla et al. | |
| 6,310,205 B1 | 10/2001 | Chasin et al. | |
| 6,319,928 B1 | 11/2001 | Chasin et al. | |
| 2003/0045533 A1 | 3/2003 | Liu et al. | |
| 2003/0187006 A1* | 10/2003 | Hagan | 514/275 |
| 2004/0242598 A1* | 12/2004 | Liu et al. | 514/263.4 |
| 2006/0052331 A1* | 3/2006 | Koch et al. | 514/45 |

FOREIGN PATENT DOCUMENTS

| | | |
|---|---|---|
| DE | 2 405 895 | 8/1974 |
| DE | 42 30 755 | 3/1994 |
| DE | 197 02 785 | 7/1998 |
| DE | 199 35 209 | 2/2001 |
| EP | 1 043 324 | 10/2000 |
| JP | 62-10085 | 1/1987 |
| JP | 64-72415 | 3/1989 |
| JP | 05-001066 | 1/1993 |
| JP | 62-240622 | 10/1997 |
| JP | 11-180982 | 7/1999 |
| JP | 11-1895877 | 7/1999 |
| JP | 2000-072773 | 3/2000 |
| JP | 200072773 A * | 3/2000 |
| JP | 2000072773 | 3/2000 |
| WO | WO 93/25517 | 12/1993 |
| WO | WO 94/14742 | 7/1994 |
| WO | WO 98/58901 | 12/1998 |
| WO | WO99/24432 | 5/1999 |
| WO | WO 99/29694 | 6/1999 |
| WO | WO 01/87281 | 11/2001 |
| WO | WO 02/098878 | 12/2002 |

OTHER PUBLICATIONS

"Hydroxamic acids" <http://www.iupac.org/goldbook/H02911.pdf> downloaded from the internet Jul. 17, 2006.*
Grant & Hackh's Chemical dictionary, $5^{th}$ edition, pp. 115, 220 (1987).*
Zhang et al., Psychopharmacology 179, 613 (2005).*
Kelley, et al., J. Med. Chem.; 1989; 32(8) pp. 1757-1763.*
T. J. Martin, "PDE4 Inhibitors—A Review of the Recent Patent Literature", IDrugs, vol. 4, No. 3, 2001, pp. 312-338.
Chalmers (TiPS vol. 17, pp. 166-172 Apr. 1996).
Thomas C. McKenzie et al., "The Gomberg-Bachmann Reaction of Purines", J. Heterocyclic Chem., May-Jun. 1987, pp. 859-881, vol. 24.
Vasu Nair et al., "Novel, Stable Congeners of Antiretroviral Compound 2', 3'—Dideoxyadenosine," J. Am. Chem. Soc., 1989, pp. 8502-8504, vol. 111.
James L. Kelley et al., "6-(Alkylamino)-9-alkylpurines. A New Class of Potential Antipsychotic Agents," J. Med. Chem., 1997, pp. 3207-3216, vol. 40.

(Continued)

*Primary Examiner*—Mark L. Berch
(74) *Attorney, Agent, or Firm*—Millen, White, Zelano, Branigan, P.C.

(57) ABSTRACT

PDE4 inhibition is achieved by novel compounds of the Formula I:

wherein $R^1$ and $R^2$ are as defined herein.

62 Claims, No Drawings

OTHER PUBLICATIONS

V. Vair, "Hydrolysis of Dideoxgenated Purine Nucleosides: Effect of Modification o f the Base Moiety", J. Org. Chem, 1990, pp. 3695-3697, vol. 55, No. 11.

H. Nagano et al., "Fluorine-Containing Potential Anticancer agents. II. Syntheses Trifuoromethylpurines and Trifluormethylthiazolopyrimidines", J. Med. Chem., 1964, pp. 215-220, vol. 7, No. 2.

Vasu Nair et al., "Inhibition of mammalian adenosine deaminase by novel functionalized 2', 3'-dideoxyadenosines", Biochim. Biophys. Acta, 1991, pp. 121-123, vol. 1078, No. 1.

International Search Report dated Jan. 23, 2004.

International Search Report dated Oct. 15, 2002.

PCT/US03/24914 International Search Report dated May 11, 2004.

Japanese Abstract No. 05-001066 dated Jan. 8, 1993.

Japanese Abstract No. 62-240622 dated Oct. 21, 1987.

Japanese Abstract No. 62-010085 dated Jan. 19, 1987.

J.J. Bourguignon, et al., "9-Benzyladenines: Potent and Selective cAMP Phosphodiesterase Inhibitors", *J. Med. Chem.*, 1997, vol. 40, No. 12, pp. 1768-1770.

J. L. Kelley, et al., "Antirhinovirus structure-activity relationships of 6-substituted-9-(4-methylbenzyl)-2-trifluoromethyl-9H-purines", *Eur. J. Med. Chem.*, 1990, vol. 25, No. 2, pp. 131-135.

E. Boichot, et al. Anti-Inflammatory Activites of a New Series of Selective Phosphodiesterase 4 Inhibitors Derived from 9-Benzyladenine[1], *The Journal of Pharm. and Exp. Thera.*, 2000, vol. 292, No. 2, pp. 647-653.

Japanese Patent Abstract No. 10-72415 dated Mar. 17, 1998.

Japanese Patent Abstract No. 11-189577 dated Jul. 13, 1999.

Japanese Patent Abstract No. 62-240622 dated Oct. 21, 1987.

Japanese Patent Abstract No. 05-001066 dated Jan. 8, 1993.

Japanese Patent Abstract No. 62-10085 dated Jan. 19, 1987.

Japanese Patent Abstract No. 2000-072773, with partial translation.

Donald V. Daniels et al., "A Semiautomated Method of the Assay of Cyclic Adenosine 5'-Monophosphate Phosphodiesterase," *Analytical Biochemistry*, 1996, pp. 367-369, vol. 236.

Mary Elizabeth Bach et al., "Age-related defects in spatial memory are correlated with defects in the late phase of hippocampal long term potentiation in vitro and are attenuated by drugs that enhance the cAMP signaling pathway", *Proc. Natl. Acad. Sci.* USA, Apr. 1999, pp. 5280-5285, vol. 96.

Raboisson et al., "Design, synthesis and structure—activity relationsips of series of 9-substituted adenine derivatives . . . " Eur. J. Med. Chem., 38, 2003, pp. 199-214.

Reimund et al., "Anti-TNF-α Properties of New 9-Benzyladenine Derivatives with Selective . . . ", Biochemical & BioPhysical, (2001), pp. 427-434.

Hiroyuki Sawanishi et al., "Selective Inhibitors of Cyclic AMP-Specific Phosphodiesterase: Heterocycle-Condensed Purines", *J. Med. Chem.*, 1997, pp. 3248-3253, vol. 40.

J.E. Sounnes et al., "Proposal for Pharmacologically Distinct Conformers of PDE4 Cyclic AMP Phosphodiesterases", *Cell Signal*, 1997, pp. 227-236. vol. 9, No. 3-4.

Roger J. Schilling et al., "A High-Throughput Assay For Cyclic Nucleotide Phosphodiesterases," *Analytical Biochemistry*, 1994, pp. 154-158, vol. 215.

James L. Kelley et al., "Synthesis and Structure- Activity Relationships of 2-Substituted-6-(dimethylamino)- 9-(4-methylbenzyl)-9H-purines with Antirhinovirus Activity," *J. Med. Chem.*, 1989, pp. 218-224, vol. 32.

Vasu Nair et al., "Synthesis Of Congeners Of Adenosine Resistant To Deamination By Adenosine Deaminase," *J. Chem. Soc Comm.*, 1989, pp. 878-879.

* cited by examiner

PHOSPHODIESTERASE 4 INHIBITORS

This application claims the benefit of U.S. Provisional Application No. 60/401,764, filed Aug. 8, 2002.

This application is related to U.S. patent application Ser. No. 10/067,996, filed Feb. 8, 2002, U.S. Provisional application Ser. No. 60/267,195, filed Feb. 8, 2001, and U.S. Provisional application Ser. No. 60/344,824, filed Jan. 7, 2002, all of which are hereby incorporated by reference in their entirety.

FIELD OF THE INVENTION

The present invention relates generally to the field of phosphodiesterase 4 (PDE4) enzyme inhibition. More specifically this invention relates to selective PDE4 inhibition by novel purine analogs, methods of preparing such compounds, compositions containing such compounds, and methods of use thereof.

BACKGROUND OF THE INVENTION

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE 1 is stimulated by $Ca^{2+}$/calmodulin. PDE 2 is cGMP-dependent, and is found in the heart and adrenals. PDE 3 is cGMP-dependent, and inhibition of this enzyme creates positive inotropic activity. PDE 4 is cAMP specific, and its inhibition causes airway relaxation, anti-inflammatory and antidepressant activity. PDE 5 appears to be important in regulating cGMP content in vascular smooth muscle, and therefore PDE 5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [See: Wang et al., Expression, Purification, and Characterization of human cAMP-Specific Phosphodiesterase (PDE4) Subtypes A, B, C, and D, *Biochem. Biophys. Res. Comm.*, 234, 320-324 (1997)] In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory. Inhibitors of PDE4 isoenzymes such as rolipram, piclamilast, CDP-840 and ariflo are powerful anti-inflammatory agents and therefore may be useful in treating diseases where inflammation is problematic such as asthma or arthritis. Further, rolipram improves the cognitive performance of rats and mice in learning paradigms.

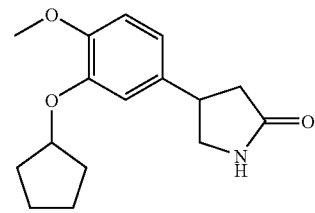

Rolipram

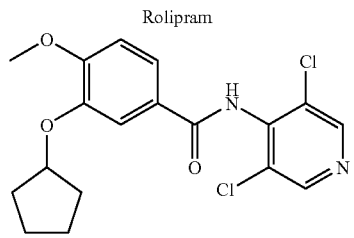

Piclamilast

In addition to such compounds as rolipram, xanthine derivatives such as pentoxifylline, denbufylline, and theophylline inhibit PDE4 and have received considerable attention of late for their cognition enhancing effects. cAMP and cGMP are second messengers that mediate cellular responses to many different hormones and neurotransmitters. Thus, therapeutically significant effects may result from PDE inhibition and the resulting increase in intracellular cAMP or cGMP in key cells, such as those located in the nervous system and elsewhere in the body.

Rolipram, previously in development as an anti-depressant, selectively inhibits the PDE4 enzyme and has become a standard agent in the classification of PDE enzyme subtypes. Early work in the PDE4 field focused on depression and inflammation, and has subsequently been extended to include indications such as dementia. [see "The PDE IV Family Of Calcium-Phosphodiesterases Enzymes," John A. Lowe, III, et al., Drugs of the Future 1992, 17(9):799-807 for a general review). Further clinical developments of rolipram and other first-generation PDE4 inhibitors were terminated due to the side effect profile of these compounds. The primary side effect in primates is emesis, while the primary side effects in rodents are testicular degranulation, weakening of vascular smooth muscle, psychotropic effects, increased gastric acid secretion and stomach erosion.

SUMMARY OF THE INVENTION

The present invention relates to novel purine compounds that inhibit PDE4 enzymes, and especially have improved side effect profiles, e.g., are relatively non-emetic, (e.g., as compared to the previously discussed prior art compounds). In particular, the present invention relates to novel 6,9-disubstituted-2-trifluoromethylpurine compounds that possess PDE4 inhibitory activity. Preferably, the compounds selectively inhibit PDE4 enzymes. The compounds of this invention at the same time facilitate entry into cells, especially cells of the nervous system.

Still further, the present invention provides methods for synthesizing compounds with such activity and selectivity as well as methods of (and corresponding pharmaceutical compositions for) treating a patient, e.g., mammals, including humans, requiring PDE inhibition, especially PDE4 inhibition, for a disease state that involves elevated intracellular PDE 4 levels or decreased cAMP levels, e.g., involving neurological syndromes, especially those states associated with memory impairment, most especially long term memory impairment, as where such memory impairment is due in part to catabolism of intracellular cAMP levels by PDE 4 enzymes, or where such memory impairment may be improved by effectively inhibiting PDE4 enzyme activity.

In a preferred aspect, the compounds of the invention improve such diseases by inhibiting PDE4 enzymes at doses which do not induce emesis.

Upon further study of the specification and appended claims, further aspects, objects and advantages of this invention will become apparent to those skilled in the art.

The present invention includes compounds of Formula I:

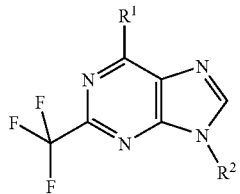

I wherein,
$R^1$ is halogen (e.g., chloro),
  dimethylamino,
  alkyl having 1 to 6 carbon atoms (e.g., ethyl), which is unsustituted or substituted one or more times by halogen, hydroxy, or combinations thereof, and wherein a —$CH_2$— group can be optionally replaced by —O—, —S—, or —$NCH_3$—, and/or one or more —$CH_2$—$CH_2$— groups can each be replaced by —CH=CH— or —C≡C—,
  cycloalkyl having 3 to 6 carbon atoms (e.g., cyclopropyl),
  cycloalkylalkyl having 4 to 7 C atoms (e.g., cyclopropylmethyl),
  methoxy, or
  pyrrolidinyl;
$R^2$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH=CH— or —C≡C—,
  alkyl ether having 3 to 12 carbon atoms,
  cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
  cycloalkylalkyl having 4 to 12 C atoms, which is unsubstituted or substituted one or more times by $C_{1-4}$ alkyl, halogenated $C_{1-4}$ alkyl, $C_{1-4}$ alkoxy, cyano, halogen, or combinations thereof,
  aryl having 6 to 14 carbon atoms (e.g., phenyl), which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, C1-4 alkylamino, di-C1-4-alkylamino, C1-4-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —$NR^3R^4$, —CO—NH—$SO_2$—$R^5$, —$SO_2$—NH—CO—$R^5$ or combinations thereof,
  arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —$NR^3R^4$, —CO—NH—$SO_2$—$R^5$, —$SO^2$—NH—CO—$R^5$ or combinations thereof,
  heteroaryl having 5 to 10 ring atoms in which at least 1 ring atom is a heteroatom (e.g., pyrimidinyl), which is unsubstituted or substituted one or more times by halogen, aryl, $C_{1-4}$ alkyl, halogenated $C_{1-4}$ alkyl, hydroxy, $C_{1-4}$-alkoxy,
  halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, —$NR^3R^4$, —CO—NH—$SO_2$—$R^5$, —$SO_2$—NH—CO—$R^5$ or combinations thereof,
  heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, —$NR^3R^4$, —CO—NH—$SO_2$—$R^5$, —$SO^2$—NH—CO—$R^5$ or combinations thereof,
  heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl),
  heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), or
  carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$- acyl, $C_{2-4}$-alkoxycarbonyl, $C_{1-4}$-alkylthio, $C_{1-4}$4-alkylsulphinyl, $C_{1-4}$-alkylsulphonyl, phenoxy, benzyloxy, —NR$^3$R$^4$, —CO—NH—SO$_2$—R$^5$, —SO$^2$—NH—CO—R$^5$ or combinations thereof;

R$^3$ is cycloalkyl having 3 to 8 carbon atoms (e.g., cyclopropyl), which is unsubstituted or substituted one or more times by halogen, $C_{1-4}$ alkyl, halogenated $C_{1-4}$ alkyl, $C_{1-4}$ alkoxy, cyano or combinations thereof, cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy, halogenated $C_{1-4}$ alkyl, halogenated $C_{1-4}$ alkoxy or combinations thereof (e.g., cyclopentylmethyl, cyclopropylmethyl, etc.), aryl having 6 to 14 carbon atoms (e.g., phenyl), which is unsubstituted or substituted one or more times by halogen, C1-4 alkyl, halogenated C1-4 alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, or combinations thereof, heteroaryl having 5 to 10 ring atoms in which at least 1 ring atom is a heteroatom (e.g., pyridinyl), which is unsubstituted or substituted one or more times by halogen, aryl, $C_{1-4}$ alkyl halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, or combinations thereof, $C_{1-4}$-alkylsulphonyl, or $C_{1-4}$-alkyl-CO—O—$C_{1-4}$-alkylene;

R$^4$ is H or alkyl having 1 to 4 carbon atoms which is straight chain or branched, and which is unsubstituted or substituted one or more times by halogen, hydroxy, cyano or combinations thereof;

R$^5$ is alkyl having 1 to 12 carbon atoms (e.g., methyl, ethyl), which is unsubstituted or substituted one or more times by halogen, hydroxy, cyano or combinations thereof, wherein one or more —CH$_2$— groups is each independently optionally replaced by —O—, —S—, or NH—, and wherein optionally one or more —CH$_2$CH$_2$— groups is replaced in each case by —CH═CH— or —C≡C—, cycloalkyl having 3 to 8 carbon atoms (e.g., cyclopropyl), which is unsubstituted or substituted one or more times by halogen, $C_{1-4}$ alkyl, halogenated $C_{1-4}$ alkyl, $C_{1-4}$ alkoxy, cyano or combinations thereof, cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy, halogenated $C_{1-4}$ alkyl, halogenated $C_{1-4}$ alkoxy or combinations thereof (e.g., cyclopentylmethyl, cyclopropylmethyl, etc.), aryl having 6 to 14 carbon atoms (e.g., phenyl), which is unsubstituted or substituted one or more times by halogen, $C_{1-4}$ alkyl, halogenated $C_{1-4}$ alkyl, hydroxy, $C_{1-4}$-alkoxy, halogenated C1-4 alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —NR$^3$R$^4$ or combinations thereof (e.g., phenyl, fluorophenyl, difluorophenyl, chlorophenyl), arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —NR$^3$R$^4$, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), heteroaryl having 5 to 10 ring atoms in which at least 1 ring atom is a heteroatom (e.g., pyridinyl), which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, or combinations thereof (thienyl, chlorothienyl, benzothienyl, chloromethylthienyl, benzothiazolyl, ethoxybenzothiazolyl, pyridyl, methylpyridyl, chloropyridyl);

heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, —NR$^3$R$^{4,5}$ or combinations thereof; and and pharmaceutically acceptable salts thereof, with the provisos that:

(a) when R$^1$ is methoxy, R$^2$ is cycloalkyl (e.g., cyclopentyl) or pyrimidinyl substituted by dialkylamino (e.g., dimethylamino); and (b) when R$^1$ is pyrrolidinyl, R$^2$ is cycloalkyl (e.g., cyclopentyl) or arylalkyl (e.g., fluorine substituted benzyl).

In accordance with a further aspect R² is in accordance with Formula I but is other than 4-methoxy-3-cyclopentyloxy-benzyl. Compare, e.g., WO 99/24432 and EP 1 043 324.

In accordance with a further aspect the compounds of Formula I are selected from the following compounds:
9-Cyclopentyl-6-N,N-dimethylamino-2-trifluoromethylpurine,
9-(2-Fluorobenzyl)-6-N,N-dimethylamino-2-trifluoromethylpurine,
6-Chloro-9-(2-fluorobenzyl)-2-trifluoromethylpurine,
6-Chloro-9-cyclopentyl-2-trifluoromethylpurine,
9-(4-(2-Methylsulfonyl)pyrimidinyl)-6-N,N-dimethylamino-2-trifluoromethylpurine [or 6-N,N-Dimethylamino-9-(4-(2-methylsulfonyl)pyrimidinyl)-2-trifluoromethylpurine],
9-(4-(2-N,N-Dimethylamino)pyrimidinyl)-6-N,N-dimethylamino-2-trifluoromethylpurine [or 6-N,N-Dimethylamino-9-(4-(2-N,N-dimethylamino)pyrimidinyl)-2-trifluoromethylpurine],
9-Cyclopentyl-6-methoxy-2-trifluoromethylpurine,
9-(4-(2-N,N-Dimethylamino)pyrimidinyl)-6-methoxy-2-trifluoromethylpurine,
9-Cyclopentyl-6-(1-pyrrolidinyl)-2-trifluoromethylpurine,
9-(2-Fluorobenzyl)-6-(1-pyrrolidinyl)-2-trifluoromethylpurine,
9-Cyclopentyl-6-methyl-2-trifluoromethylpurine,
9-(2-Fluorobenzyl)-6-methyl-2-trifluoromethylpurine,
9-Cyclopentyl-6-ethyl-2-trifluoromethylpurine,
9-(2-Fluorobenzyl)-6-ethyl-2-trifluoromethylpurine [or 6-Ethyl-9-(2-fluorobenzyl)-2-trifluoromethylpurine],
9-Phenyl-6-ethyl-2-trifluoromethylpurine [or 6-Ethyl-9-Phenyl-2-trifluoromethylpurine],
6-Ethyl-9-(3-methoxyphenyl)-2-trifluoromethylpurine,
6-Ethyl-9-(2-methoxyphenyl)-2-trifluoromethylpurine,
9-Cyclopentyl-6-(2-propyl)-2-trifluoromethylpurine,
6-Ethyl-9-(3-methylsulfonylphenyl)-2-trifluoromethylpurine,
6-Ethyl-9-(3-methylsulfinylphenyl)-2-trifluoromethylpurine,
6-(1-Butyl)-9-cyclopentyl-2-trifluoromethylpurine
9-Cyclopentyl-6-(1-propyl)-2-trifluoromethylpurine,
9-(2,3-Difluorobenzyl)-6-ethyl-2-trifluoromethylpurine,
6-Ethyl-9-(3-methylbenzyl)-2-trifluoromethylpurine,
6-Ethyl-9-(3-methoxybenzyl)-2-trifluoromethylpurine,
9-(2,4-Difluorobenzyl)-6-ethyl-2-trifluoromethylpurine,
9-(3-Cyanophenyl)-6-ethyl-2-trifluoromethylpurine,
9-(2,3-Dichlorophenyl)-6-ethyl-2-trifluoromethylpurine,
9-(4-Chlorophenyl)-6-ethyl-2-trifluoromethylpurine,
6-Ethyl-9-(2-fluorophenyl)-2-trifluoromethylpurine,
6-Ethyl-9-(3-fluorophenyl)-2-trifluoromethylpurine,
9-(4-Benzyloxyphenyl)-6-ethyl-2-trifluoromethylpurine,
6-Ethyl-9-(3-methylthiophenyl)-2-trifluoromethylpurine,
6-Ethyl-9-(3-methylphenyl)-2-trifluoromethylpurine,
6-Ethyl-9-(4-methylphenyl)-2-trifluoromethylpurine,
6-Ethyl-9-(4-fluorophenyl)-2-trifluoromethylpurine,
9-(2-Chlorophenyl)-6-ethyl-2-trifluoromethylpurine,
6-Ethyl-9-(4-pyridyl)-2-trifluoromethylpurine,
6-Ethyl-9-(4-methoxyphenyl)-2-trifluoromethylpurine,
9-(3-Chlorophenyl)-6-ethyl-2-trifluoromethylpurine,
9-(3-Chloro-4-pyridyl)-6-ethyl-2-trifluoromethylpurine,
6-Ethyl-9-(2-methyl-4-pyridyl)-2-trifluoromethylpurine,
6-Ethyl-9-(3-methyl-4-pyridyl)-2-trifluoromethylpurine,
6-Ethyl-9-(3-methoxy-4-pyridyl)-2-trifluoromethylpurine,
6-Ethyl-9-(3-ethylsulfonylphenyl)-2-trifluoromethylpurine,
6-Ethyl-9-(3-trifluoromethoxyphenyl)-2-trifluoromethylpurine,
6-Ethyl-9-(3-methoxycarbonylphenyl)-2-trifluoromethylpurine
6-Ethyl-9-(4-methoxycarbonylphenyl)-2-trifluoromethylpurine
6-Ethyl-9-(4-hydroxyphenyl)-2-trifluoromethylpurine,
9-(3-Aminomethylphenyl)-6-ethyl-2-trifluoromethylpurine,
9-(3-Carboxyphenyl)-6-ethyl-2-trifluoromethylpurine,
9-(4-Carboxyphenyl)-6-ethyl-2-trifluoromethylpurine,
6-Ethyl-9-(3-methylsulfonylaminocarbonylphenyl)-2-trifluoromethylpurine,
pharmaceutically acceptable salts thereof.

In addition, the present invention includes compounds of Formula I':

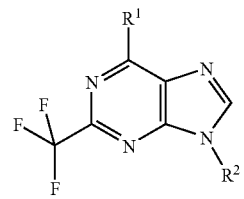

I' wherein,
R¹ is halogen (e.g., chloro),
  dimethylamino,
  alkyl having 1 to 6 carbon atoms (e.g., ethyl), which is unsubstituted or substituted one or more times by halogen, hydroxy, or combinations thereof, and wherein a —CH₂— group can be optionally replaced by —O—, —S—, or —NCH₃—, and/or one or more CH₂—CH₂— groups can each be replaced by —CH=CH— or —C≡C—,
  cycloalkyl having 3 to 6 carbon atoms (e.g., cyclopropyl),
  cycloalkylalkyl having 4 to 7 C atoms (e.g., cyclopropylmethyl),
  methoxy, or
  pyrrolidinyl;
R² is alkyl having 1 to 12 carbon atoms, which is unsubstituted or substituted one or more times by halogen, hydroxy, cyano or combinations thereof, wherein one or more —CH₂— groups is each independently optionally replaced by —O—, —S—, or —NH—, and wherein optionally one or more —CH₂CH₂— groups is replaced in each case by —CH=CH— or —C≡C—,
  alkyl ether having 3 to 12 carbon atoms,
  cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
  cycloalkylalkyl having 4 to 12 C atoms, which is unsubstituted or substituted one or more times by $C_{1-4}$ alkyl, halogenated $C_{1-4}$ alkyl, $C_{1-4}$ alkoxy, cyano, halogen, or combinations thereof,
  aryl having 6 to 14 carbon atoms (e.g., phenyl), which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —NR³R⁴ or combinations thereof, arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, heteroaryl having 5 to 10 ring atoms in which at least 1 ring atom is a heteroatom (e.g., pyrimidinyl), which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, —NR$^3$R$^4$ or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), or carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof;

R$^3$ is cycloalkyl having 3 to 8 carbon atoms (e.g., cyclopropyl), which is unsubstituted or substituted one or more times by halogen, $C_{1-4}$ alkyl, halogenated $C_{1-4}$ alkyl, $C_{1-4}$ alkoxy, cyano or combinations thereof, aryl having 6 to 14 carbon atoms. (e.g., phenyl), which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, or combinations thereof, heteroaryl having 5 to 10 ring atoms in which at least 1 ring atom is a heteroatom (e.g., pyridinyl), which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, or combinations thereof, $C_{1-4}$-alkylsulphonyl, or $C_{1-4}$-alkyl-CO—O—$C_{1-4}$-alkylene; and R$^4$ is H or alkyl having 1 to 4 carbon atoms which is straight chain or branched; and pharmaceutically acceptable salts thereof, with the provisos that:
(a) when R$^1$ is methoxy, R$^2$ is cycloalkyl (e.g., cyclopentyl) or pyrimidinyl substituted by dialkylamino (e.g., dimethylamino); and
(b) when R$^1$ is pyrrolidinyl, R$^2$ is cycloalkyl (e.g., cyclopentyl) or arylalkyl (e.g., fluorine substituted benzyl).

In accordance with a further aspect R$^2$ is in accordance with Formula I' but is other than 4-methoxy-3-cyclopentyloxy-benzyl. Compare, e.g., WO 99/24432 and EP 1 043 324.

In accordance with a further aspect the compounds of Formula I' are selected from the following compounds:

9-Cyclopentyl-6-N,N-dimethylamino-2-trifluoromethylpurine,
9-(2-Fluorobenzyl)-6-N,N-dimethylamino-2-trifluoromethylpurine,
6-Chloro-9-(2-fluorobenzyl)-2-trifluoromethylpurine,
6-Chloro-9-cyclopentyl-2-trifluoromethylpurine,
9-(4-(2-Methylsulfonyl)pyrimidinyl)-6-N,N-dimethylamino-2-trifluoromethylpurine,
9-(4-(2-N,N-Dimethylamino)pyrimidinyl)-6-N,N-dimethylamino-2-trifluoromethylpurine,
9-Cyclopentyl-6-methoxy-2-trifluoromethylpurine,
9-(4-(2-N,N-Dimethylamino)pyrimidinyl)-6-methoxy-2-trifluoromethylpurine,
9-Cyclopentyl-6-(1-pyrrolidinyl)-2-trifluoromethylpurine,
9-(2-Fluorobenzyl)-6-(1-pyrrolidinyl)-2-trifluoromethylpurine,
9-Cyclopentyl-6-methyl-2-trifluoromethylpurine,
9-(2-Fluorobenzyl)-6-methyl-2-trifluoromethylpurine,
9-Cyclopentyl-6-ethyl-2-trifluoromethylpurine,
9-(2-Fluorobenzyl)-6-ethyl-2-trifluoromethylpurine,
9-Phenyl-6-ethyl-2-trifluoromethylpurine,
6-Ethyl-9-(3-methoxyphenyl)-2-trifluoromethylpurine,
6-Ethyl-9-(2-methoxyphenyl)-2-trifluoromethylpurine, and
9-Cyclopentyl-6-(2-propyl)-2-trifluoromethylpurine.

The compounds of the present invention are effective in inhibiting, or modulating the activity of PDE4 in animals, e.g., mammals, especially humans. These compounds exhibit neurological activity, especially where such activity affects cognition, including long term memory. These compounds will also be effective in treating diseases where decreased cAMP levels are involved. This includes but is not limited to inflammatory diseases. These compounds may also function as antidepressants, or be useful in treating cognitive and negative symptoms of schizophrenia.

In accordance with the method aspect of the invention, there is provided a method of treating a patient (e.g., a mammal such as a human) suffering from a disease state (e.g., memory impairment, inflammatory diseases, depression, etc.) involving decreased cAMP levels and/or increased intracellular PDE4 levels, comprising administering to the patient a compound according to Formula I:

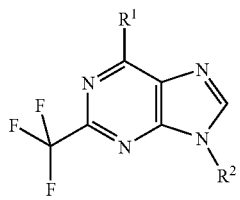

wherein, $R^1$ is halogen (e.g., chloro),
   dimethylamino,
   alkyl having 1 to 6 carbon atoms (e.g., ethyl), which is unsustituted or substituted one or more times by halogen, hydroxy, or combinations thereof, and wherein a —$CH_2$— group can be optionally replaced by —O—, —S—, or —$NCH_3$—, and/or one or more —$CH_2$—$CH_2$— groups can each be replaced by —CH=CH— or —C≡C—,
   cycloalkyl having 3 to 6 carbon atoms (e.g., cyclopropyl),
   cycloalkylalkyl having 4 to 7 C atoms (e.g., cyclopropylmethyl),
   methoxy, or
   pyrrolidinyl;

$R^2$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH=CH— or —C≡C—,
   alkyl ether having 3 to 12 carbon atoms,
   cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
   cycloalkylalkyl having 4 to 12 C atoms, which is unsubstituted or substituted one or more times by $C_{1-4}$ alkyl, halogenated $C_{1-4}$ alkyl, $C_{1-4}$ alkoxy, cyano, halogen, or combinations thereof,
   aryl having 6 to 14 carbon atoms (e.g., phenyl), which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —$NR^3R^4$, —CO—NH—$SO_2$—$R^5$, —$SO^2$—NH—CO—$R^5$ or combinations thereof,
   arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$-alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —$NR^3R^4$, —CO—NH—$SO_2$—$R^5$, —$SO^2$—NH—CO—$R^5$ or combinations thereof,
   heteroaryl having 5 to 10 ring atoms in which at least 1 ring atom is a heteroatom (e.g., pyrimidinyl), which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, —$NR^3R^4$, —CO—NH—$SO_2$—$R^5$, —$SO^2$—NH—CO—$R^5$ or combinations thereof,
   heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, —$NR^3R^4$, —CO—NH—$SO_2$—$R^5$, —$SO^2$—NH—CO—$R^5$ or combinations thereof,
   heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl),
   heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), or
   carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —$NR^3R^4$, —CO—NH—$SO_2$—$R^5$, —$SO^2$—NH—CO—$R^5$ or combinations thereof;

$R^3$ is cycloalkyl having 3 to 8 carbon atoms (e.g., cyclopropyl), which is unsubstituted or substituted one or more times by halogen, $C_{1-4}$ alkyl, halogenated $C_{1-4}$ alkyl, $C_{1-4}$ alkoxy, cyano or combinations thereof, cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy, halogenated $C_{1-4}$ alkyl, halogenated $C_{1-4}$ alkoxy or combinations thereof (e.g., cyclopentylmethyl, cyclopropylmethyl, etc.), aryl having 6 to 14 carbon atoms (e.g., phenyl), which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$4-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, or combinations thereof, heteroaryl having 5 to 10 ring atoms in which at least 1 ring atom is a heteroatom (e.g., pyridinyl), which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, or combinations thereof, $C_{1-4}$-alkylsulphonyl, or $C_{1-4}$-alkyl-CO—O—$C_{1-4}$-alkylene;

$R^4$ is H or alkyl having 1 to 4 carbon atoms which is straight chain or branched, and which is unsubstituted or substituted one or more times by halogen, hydroxy, cyano or combinations thereof;

$R^5$ is alkyl having 1 to 12 carbon atoms (e.g., methyl, ethyl), which is unsubstituted or substituted one or more times by halogen, hydroxy, cyano or combinations thereof, wherein one or more —$CH_2$— groups is each independently optionally replaced by —O—, —S—, or NH—, and wherein optionally one or more —$CH_2CH_2$— groups is replaced in each case by —CH=CH— or —C≡C—, cycloalkyl having 3 to 8 carbon atoms (e.g., cyclopropyl), which is unsubstituted or substituted one or more times by halogen, C1-4 alkyl, halogenated C1-4 alkyl, C1-4 alkoxy, cyano or combinations thereof, cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy, halogenated $C_{1-4}$ alkyl, halogenated $C_{1-4}$ alkoxy or combinations thereof (e.g., cyclopentylmethyl, cyclopropylmethyl, etc.), aryl having 6 to 14 carbon atoms (e.g., phenyl), which is unsubstituted or substituted one or more times by halogen, C1-4 alkyl, halogenated C1-4 alkyl, hydroxy, C1-4-alkoxy, halogenated C1-4 alkoxy, nitro, methylenedioxy, ethylenedioxy, amino, C1-4 alkylamino, di-C1-4-alkylamino, C1-4-hydroxyalkyl, C1-4-hydroxyalkoxy, carboxy, cyano, hydroxamic acid, carboxamide, C2-4-acyl, C2-4-alkoxycarbonyl, C1-4-alkylthio, C1-4-alkylsulphinyl, C1-4-alkylsulphonyl, phenoxy, benzyloxy, —NR3R4 or combinations thereof (e.g., phenyl, fluorophenyl, difluorophenyl, chlorophenyl), arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —$NR^3R^4$, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), heteroaryl having 5 to 10 ring atoms in which at least 1 ring atom is a heteroatom (e.g., pyridinyl), which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, or combinations thereof (thienyl, chlorothienyl, benzothienyl, chloromethylthienyl, benzothiazolyl, ethoxybenzothiazolyl, pyridyl, methylpyridyl, chloropyridyl), heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, —$NR^3R^{4,5}$ or combinations thereof; and and pharmaceutically acceptable salts thereof, with the provisos that:

(a) when $R^1$ is methoxy, $R^2$ is cycloalkyl (e.g., cyclopentyl) or pyrimidinyl substituted by dialkylamino (e.g., dimethylamino); and (b) when $R^1$ is pyrrolidinyl, $R^2$ is cycloalkyl (e.g., cyclopentyl) or arylalkyl (e.g., fluorine substituted benzyl).

In accordance with a further method aspect $R^2$ is in accordance with Formula I but is other than 4-methoxy-3-cyclopentyloxy-benzyl. Compare, e.g., WO 99/24432 and EP 1 043 324.

In accordance with the method aspect of the invention, there is provided a method of treating a patient (e.g., a mammal such as a human) suffering from a disease state (e.g., memory impairment, inflammatory diseases, depression, etc.) involving decreased cAMP levels and/or increased intracellular PDE4 levels, comprising administering to the patient a compound according to Formula I wherein said compound is selected from the following compounds:

9-Cyclopentyl-6-N,N-dimethylamino-2-trifluoromethylpurine,
9-(2-Fluorobenzyl)-6-N,N-dimethylamino-2-trifluoromethylpurine,
6-Chloro-9-(2-fluorobenzyl)-2-trifluoromethylpurine,
6-Chloro-9-cyclopentyl-2-trifluoromethylpurine,
9-(4-(2-Methylsulfonyl)pyrimidinyl)-6-N,N-dimethylamino-2-trifluoromethylpurine [or 6-N,N-Dimethylamino-9-(4-(2-methylsulfonyl)pyrimidinyl)-2-trifluoromethylpurine],
9-(4-(2-N,N-Dimethylamino)pyrimidinyl)-6-N,N-dimethylamino-2-trifluoromethylpurine [or 6-N,N-Dimethylamino-9-(4-(2-N,N-dimethylamino)pyrimidinyl)-2-trifluoromethylpurine],
9-Cyclopentyl-6-methoxy-2-trifluoromethylpurine,
9-(4-(2-N,N-Dimethylamino)pyrimidinyl)-6-methoxy-2-trifluoromethylpurine,
9-Cyclopentyl-6-(1-pyrrolidinyl)-2-trifluoromethylpurine,
9-(2-Fluorobenzyl)-6-(1-pyrrolidinyl)-2-trifluoromethylpurine,
9-Cyclopentyl-6-methyl-2-trifluoromethylpurine,
9-(2-Fluorobenzyl)-6-methyl-2-trifluoromethylpurine,
9-Cyclopentyl-6-ethyl-2-trifluoromethylpurine,
9-(2-Fluorobenzyl)-6-ethyl-2-trifluoromethylpurine [or 6-Ethyl-9-(2-fluorobenzyl)-2-trifluoromethylpurine],
9-Phenyl-6-ethyl-2-trifluoromethylpurine [or 6-Ethyl-9-Phenyl-2-trifluoromethylpurine],
6-Ethyl-9-(3-methoxyphenyl)-2-trifluoromethylpurine,
6-Ethyl-9-(2-methoxyphenyl)-2-trifluoromethylpurine,
9-Cyclopentyl-6-(2-propyl)-2-trifluoromethylpurine,
6-Ethyl-9-(3-methylsulfonylphenyl)-2-trifluoromethylpurine,
6-Ethyl-9-(3-methylsulfinylphenyl)-2-trifluoromethylpurine,
6-(1-Butyl)-9-cyclopentyl-2-trifluoromethylpurine
9-Cyclopentyl-6-(1-propyl)-2-trifluoromethylpurine,
9-(2,3-Difluorobenzyl)-6-ethyl-2-trifluoromethylpurine,
6-Ethyl-9-(3-methylbenzyl)-2-trifluoromethylpurine,
6-Ethyl-9-(3-methoxybenzyl)-2-trifluoromethylpurine,
9-(2,4-Difluorobenzyl)-6-ethyl-2-trifluoromethylpurine,
9-(3-Cyanophenyl)-6-ethyl-2-trifluoromethylpurine,
9-(2,3-Dichlorophenyl)-6-ethyl-2-trifluoromethylpurine,
9-(4-Chlorophenyl)-6-ethyl-2-trifluoromethylpurine,
6-Ethyl-9-(2-fluorophenyl)-2-trifluoromethylpurine,
6-Ethyl-9-(3-fluorophenyl)-2-trifluoromethylpurine,
9-(4-Benzyloxyphenyl)-6-ethyl-2-trifluoromethylpurine,
6-Ethyl-9-(3-methylthiophenyl)-2-trifluoromethylpurine,
6-Ethyl-9-(3-methylphenyl)-2-trifluoromethylpurine,
6-Ethyl-9-(4-methylphenyl)-2-trifluoromethylpurine,
6-Ethyl-9-(4-fluorophenyl)-2-trifluoromethylpurine,
9-(2-Chlorophenyl)-6-ethyl-2-trifluoromethylpurine,
6-Ethyl-9-(4-pyridyl)-2-trifluoromethylpurine,
6-Ethyl-9-(4-methoxyphenyl)-2-trifluoromethylpurine,
9-(3-Chlorophenyl)-6-ethyl-2-trifluoromethylpurine,
9-(3-Chloro-4-pyridyl)-6-ethyl-2-trifluoromethylpurine,
6-Ethyl-9-(2-methyl-4-pyridyl)-2-trifluoromethylpurine,
6-Ethyl-9-(3-methyl-4-pyridyl)-2-trifluoromethylpurine,
6-Ethyl-9-(3-methoxy-4-pyridyl)-2-trifluoromethylpurine,
6-Ethyl-9-(3-ethylsulfonylphenyl)-2-trifluoromethylpurine,
6-Ethyl-9-(3-trifluoromethoxyphenyl)-2-trifluoromethylpurine,
6-Ethyl-9-(3-methoxycarbonylphenyl)-2-trifluoromethylpurine
6-Ethyl-9-(4-methoxycarbonylphenyl)-2-trifluoromethylpurine
6-Ethyl-9-(4-hydroxyphenyl)-2-trifluoromethylpurine,
9-(3-Aminomethylphenyl)-6-ethyl-2-trifluoromethylpurine,
9-(3-Carboxyphenyl)-6-ethyl-2-trifluoromethylpurine,
9-(4-Carboxyphenyl)-6-ethyl-2-trifluoromethylpurine,
6-Ethyl-9-(3-methylsulfonylaminocarbonylphenyl)-2-trifluoromethylpurine,
pharmaceutically acceptable salts thereof.

In accordance with the method aspect of the invention, there is provided a method of treating a patient (e.g., a mammal such as a human) suffering from a disease state (e.g., memory impairment, inflammatory diseases, depression, etc.) involving decreased cAMP levels and/or increased intracellular PDE4 levels, comprising administering to the patient a compound according to Formula I':

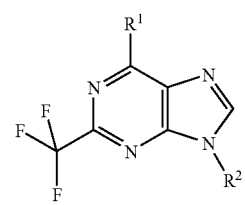

wherein,
$R^1$ is halogen (e.g., chloro),
dimethylamino,
alkyl having 1 to 6 carbon atoms (e.g., ethyl), which is unsubstituted or substituted one or more times by halogen, hydroxy, or combinations thereof, and wherein a —$CH_2$— group can be optionally replaced by —O—, —S—, or —$NCH_3$—, and/or one or more —$CH_2$—$CH_2$— groups can each be replaced by —CH=CH— or —C≡C—,
cycloalkyl having 3 to 6 carbon atoms (e.g., cyclopropyl),
cycloalkylalkyl having 4 to 7 C atoms (e.g., cyclopropylmethyl),
methoxy, or
pyrrolidinyl;
$R^2$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH=CH— or —C≡C—,
alkyl ether having 3 to 12 carbon atoms,
cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
cycloalkylalkyl having 4 to 12 C atoms, which is unsubstituted or substituted one or more times by $C_{1-4}$ alkyl, halogenated $C_{1-4}$ alkyl, $C_{1-4}$ alkoxy, cyano, halogen, or combinations thereof,
aryl having 6 to 14 carbon atoms (e.g., phenyl), which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —NR$^3$R$^4$ or combinations thereof, arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, heteroaryl having 5 to 10 ring atoms in which at least 1 ring atom is a heteroatom (e.g., pyrimidinyl), which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, —NR$^3$R$^4$ or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), or carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof;

R$^3$ is-cycloalkyl having 3 to 8 carbon atoms (e.g., cyclopropyl), which is unsubstituted or substituted one or more times by halogen, $C_{1-4}$ alkyl, halogenated $C_{1-4}$ alkyl, $C_{1-4}$ alkoxy, cyano or combinations thereof, aryl having 6 to 14 carbon atoms (e.g., phenyl), which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, or combinations thereof, heteroaryl having 5 to 10 ring atoms in which at least 1 ring atom is a heteroatom (e.g., pyridinyl), which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, morpholinyl, piperazinyl, or-combinations thereof, $C_{1-4}$-alkylsulphonyl, or $C_{1-4}$-alkyl-CO—O—$C_{1-4}$-alkylene; and R$^4$ is H or alkyl having 1 to 4 carbon atoms which is straight chain or branched; and pharmaceutically acceptable salts thereof, with the provisos that:
(a) when R$^1$ is methoxy, R$^2$ is cycloalkyl (e.g., cyclopentyl) or pyrimidinyl substituted by dialkylamino (e.g., dimethylamino); and
(b) when R$^1$ is pyrrolidinyl, R$^2$ is cycloalkyl (e.g., cyclopentyl) or arylalkyl (e.g., fluorine substituted benzyl).

In accordance with a further method aspect R$^2$ is in accordance with Formula I' but is other than 4-methoxy-3-cyclopentyloxy-benzyl. Compare, e.g., WO 99/24432 and EP 1 043 324.

In accordance with the method aspect of the invention, there is provided a method of treating a patient (e.g., a mammal such as a human) suffering from a disease state (e.g., memory impairment, inflammatory diseases, depression, etc.) involving decreased cAMP levels and/or increased intracellular PDE4 levels, comprising administering to the patient a compound according to Formula I' wherein said compound is selected from the following compounds:

9-Cyclopentyl-6-N,N-dimethylamino-2-trifluoromethylpurine, 9-(2-Fluorobenzyl)-6-N,N-dimethylamino-2-trifluoromethylpurine, 6-Chloro-9-(2-fluorobenzyl)-2-trifluoromethylpurine, 6-Chloro-9-cyclopentyl-2-trifluoromethylpurine, 9-(4-(2-Methylsulfonyl)pyrimidinyl)-6-N,N-dimethylamino-2-trifluoromethylpurine, 9-(4-(2-N,N-Dimethylamino)pyrimidinyl)-6-N,N-dimethylamino-2-trifluoromethylpurine, 9-Cyclopentyl-6-methoxy-2-trifluoromethylpurine, 9-(4-(2-N,N-Dimethylamino)pyrimidinyl)-6-methoxy-2-trifluoromethylpurine, 9-Cyclopentyl-6-(1-pyrrolidinyl)-2-trifluoromethylpurine, 9-(2-Fluorobenzyl)-6-(1-pyrrolidinyl)-2-trifluoromethylpurine,
9-Cyclopentyl-6-methyl-2-trifluoromethylpurine,
9-(2-Fluorobenzyl)-6-methyl-2-trifluoromethylpurine,
9-Cyclopentyl-6-ethyl-2-trifluoromethylpurine,
9-(2-Fluorobenzyl)-6-ethyl-2-trifluoromethylpurine,
9-Phenyl-6-ethyl-2-trifluoromethylpurine,
6-Ethyl-9-(3-methoxyphenyl)-2-trifluoromethylpurine,
6-Ethyl-9-(2-methoxyphenyl)-2-trifluoromethylpurine, and
9-Cyclopentyl-6-ethyl-2-trifluoromethylpurine Assays for determining PDE inhibiting activity as well as selectivity of PDE 4 inhibiting activity and selectivity of inhibiting PDE 4 isoenzymes are known within the art. See, e.g., U.S. Pat. No. 6,136,821, the disclosure of which is incorporated herein by reference.

Halogen herein refers to F, Cl, Br, and I. Preferred halogens are F and Cl.

Alkyl, as a group or substituent per se or as part of a group or substituent (e.g., alkylamino, trialkylsilyloxy, aminoalkyl, hydroxyalkyl), means a straight-chain or branched-chain aliphatic hydrocarbon radical having 1 to 12 carbon atoms, preferably 1 to 8 carbon atoms, especially 1 to 4 carbon atoms.

Alkyl radicals for $R^1$ have up to 5 carbon atoms, preferably 1 to 4 carbon atoms, especially 1 to 3 carbon atoms. Suitable alkyl groups for $R^1$ include methyl, ethyl, propyl, isopropyl, butyl, isopropyl and pentyl. Other examples of suitable alkyl groups for $R^1$ include 1-, 2- or 3-methylbutyl, 1,1-, 1,2- or 2,2-dimethylpropyl and 1-ethylpropyl.

Alkyl radicals for $R^2$ have up to 12 carbon atoms, preferably 3 to 8 carbon atoms, especially 3 to 6 carbon atoms. Suitable alkyl groups for $R^2$ include those listed above for $R^1$ as well as hexyl, heptyl, octyl, nonyl, decyl, undecyl, dodecyl, 1-, 2-, 3- or 4-methylpentyl, tert-butyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, for example, halogens, oxo, hydroxy, $C_{1-4}$-alkoxy, halogenated $C_{1-4}$-alkoxy, and/or cyano. Halogens are preferred substituents, especially F and Cl.

Alkoxy groups means alkyl-O-groups in which the alkyl portion is in accordance with the previous discussion. Suitable alkoxy groups are methoxy, ethoxy, propoxy and butoxy, pentoxy, hexoxy, heptoxy, octoxy and trifluoromethoxy. Preferred alkoxy groups are methoxy and ethoxy. Similarly, alkoxycarbonyl means alkyl —O—CO— in which the alkyl portion is in accordance with the previous discussion. Examples include methoxycarbonyl, ethoxycarbonyl, propoxycarbonyl, and tert-butoxycarbonyl.

Alkenyl refers to straight-chain or branched-chain aliphatic radicals containing 2 to 12 carbon atoms in which one or more —CH$_2$—CH$_2$— structures are each replaced by —CH=CH—. Suitable alkenyl groups are ethenyl, 1-propenyl, 2-methylethenyl, 1-butene, 2-butene, 1-pentenyl, and 2-pentenyl.

Alkynyl refers to straight-chain or branched-chain aliphatic radicals containing 2 to 12 carbon atoms in which one or more —CH$_2$—CH$_2$— structures are each replaced by —C≡C—. Suitable alkynyl groups are ethynyl, propynyl, 1-butynyl, and 2-butynyl.

Cycloalkyl means a monocyclic, bicyclic or tricyclic nonaromatic saturated hydrocarbon radical. Cycloalkyl radicals for $R^1$ have 3 to 6 carbon atoms, preferably 3 to 5 carbon atoms, especially 3 carbon atoms. Suitable cycloalkyl groups for $R^1$ include cyclopropyl, cyclobutyl, cyclopentyl and cyclohexyl. Cycloalkyl radicals for $R^2$ have 3 to 12 carbon atoms, preferably 3 to 10 carbon atoms, especially 4 to 8 carbon atoms. Suitable cycloalkyl groups for $R^2$ include those listed above for $R^1$ as well as cycloheptyl, cyclooctyl, cyclononyl, norbornyl, 1-decalin, adamant-1-yl, and adamant-2-yl. Other suitable cycloalkyl groups for $R^2$ include spiro[2,4]heptyl, spiro[2.5]octyl, bicyclo [5.1.0]octyl, bicyclo[2.2.0]hexyl, spiro[3.3]heptyl, and bicyclo[4.2.0]octyl.

The cycloalkyl group can be substituted. For example, it can be substituted by halogens, $C_{1-4}$-alkyls, $C_{1-4}$-halogenated alkyls, $C_{1-4}$-alkoxy and/or cyano.

Cycloalkylalkyl refers to cycloalkyl-alkyl radicals in which the cycloalkyl and alkyl portions are in accordance with previous discussions. Suitable examples include cyclopropylmethyl and cyclopentylmethyl.

Alkyl ethers refer to $C_3$ to $C_{12}$ alkoxyalkyl radicals. Suitable alkyl ether groups include methoxyethyl, ethoxyethyl, and methoxypropyl.

Aryl, as a group or substituent per se or as part of a group or substituent, refers to an aromatic carbocyclic radical containing 6 to 14 carbon atoms, preferably 6 to 12 carbon atoms, especially 6 to 10 carbon atoms. Suitable aryl groups include phenyl, naphthyl and biphenyl. Substituted aryl groups include the above-described aryl groups which are substituted one or more times by, for example, by halogen, $C_{1-4}$-alkyl, $C_{1-4}$-halogenated alkyl, hydroxy, $C_{1-4}$-alkoxy, $C_{1-4}$-halogenated alkoxy, nitro, methylenedioxy, ethylenedioxy, amino, $C_{1-4}$-alkylamino, di-$C_{1-4}$-alkylamino, $C_{1-4}$-hydroxyalkyl, $C_{1-4}$-hydroxyalkoxy, carboxy, cyano, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl and phenoxy.

Arylalkyl refers to an aryl-alkyl-radical in which the aryl and alkyl portions are in accordance with the previous descriptions. Preferably, the aryl portion has 6 to 10 carbon atoms and the alkyl portion, which is straight-chained or branched, has 1 to 6 carbon atoms, preferably 1 to 3 carbon atoms. The aryl portion can be substituted by the substituents described above for aryl groups and the alkyl portion can be substituted by oxo, halogens, cyano or combinations thereof. Suitable examples include benzyl, 1-phenethyl, 2-phenethyl, phenpropyl, fluorobenzyl, chlorobenzyl, methoxybenzyl, methylbenzyl and cyanobenzyl.

Heteroaryl refers to an aromatic heterocyclic group having one or two rings and a total number of 5 to 10 ring atoms wherein at least one of the ring atoms is a heteroatom. Preferably, the heteroaryl group contains 1 to 3, especially 1 or 2, hetero-ring atoms which are selected from N, O and S. Suitable heteroaryl groups include furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, thiadiazolyl, pyridyl, pyridazinyl, pyrimidinyl, benzofuranyl, isobenzofuranyl, thionaphthenyl, isothionaphthenyl, indolyl, isoindolyl, indazolyl, benzoisoxazolyl, benzoxazolyl, benzothiazolyl, benzoisothiazolyl, purinyl, benzopyranyl, quinolinyl, isoquinolinyl, cinnolinyl, quinazolinyl, naphthyridinyl, and benzoxazinyl, e.g., 2-thienyl, 3-thienyl, 2-, 3- or 4-pyridyl, 2-, 3-, 4-, 5-, 6-, 7- or 8-quinolinyl, and 1-, 3-, 4-, 5-, 6-, 7- or 8-isoquinolinyl.

Substituted heteroaryl refers to the heteroaryl groups described above which are substituted in one or more places by, for example, halogen, hydroxyl, aryl, alkyl, alkoxy, carboxy, methylene, cyano, trifluoromethyl, nitro, oxo, amino, alkylamino, and dialkylamino.

Heteroarylalkyl refers to a heteroaryl-alkyl-group wherein the heteroaryl and alkyl portions are in accordance with the previous discussions. Suitable examples are pyridylmethyl, thienylmethyl, pyrimidinylmethyl, pyrazinylmethyl, and isoquinolinylmethyl.

Heterocycles are non-aromatic cyclic groups containing at least one hetero-ring atom, preferably selected from N, S and O, for example, 3-tetrahydrofuranyl, piperidinyl, imidazolinyl, imidazolidinyl, pyrrolinyl, pyrrolidinyl, morpholinyl, piperazinyl, and indolinyl.

Heterocycle-alkyl refers to a heterocycle-alkyl-group wherein the heterocyclic and alkyl portions are in accordance with the previous discussions. Suitable examples are piperidinyl-ethyl and pyrrolinyl-methyl.

Carbocycles are non-aromatic monocyclic or bicyclic structures containing 5 to 14 carbon atoms, preferably 6 to 10 carbon atoms. Suitable examples are cyclopentenyl, cyclohexenyl, cyclohexadienyl, tetrahydronaphthenyl and indan-2-yl.

Acyl refers to alkanoyl radicals having 1 to 6 carbon atoms in which the alkyl portion can be substituted by halogen, alkyl, aryl and/or alkoxy, or aroyl radicals having 7 to 15 carbon atoms in which the aryl portion can be substituted by, for example, halogen, alkyl and/or alkoxy. Suitable acyl groups include formyl, acetyl, propionyl, butanoyl and benzoyl.

Substituted radicals preferably have 1 to 3 substituents, especially 1 to 2 substituents.

$R^1$ is preferably Cl, dimethylamino, methoxy, pyrrolidinyl, or alkyl such as methyl, ethyl or isopropyl.

$R^2$ is preferably cycloalkyl (e.g., cyclopentyl), aryl (e.g., phenyl), arylakyl (e.g., benzyl), or heteroaryl (e.g., pyrimidinyl). In particular, $R^2$ is cyclopentyl, phenyl which is unsubstituted or substituted one or more times by, e.g., alkoxy, benzyl which is unsubstituted or substituted by, e.g., F, or pyrimidinyl which is unsubstituted or substituted by, for example, alkylsulfonyl, or dialkylamino.

When $R^2$ is aryl substituted by —CO—NH—SO$_2$—$R^5$ and/or —SO$_2$—NH—CO—$R^5$, the aryl group is preferably phenyl and $R^5$ is preferably alkyl which is substituted or unsubstituted, e.g., methyl and ethyl.

In addition, preferred PDE4 inhibitors, in accordance with the invention, are compounds described by subformulas Ia-Ij, which correspond to Formula I, but exhibit the following preferred groups:

$R^1$ is Cl, dimethylamino, methyl, ethyl, isopropyl, propyl, methoxy, or pyrrolidinyl; and
$R^2$ is cycloalkyl, aryl, arylakyl, or heteroaryl, which in each case is unsubstituted or substituted,
with the provisos that:
(a) when $R^1$ is methoxy, $R^2$ is cycloalkyl or pyrimidinyl substituted by dialkylamino; and
(b) when $R^1$ is pyrrolidinyl, $R^2$ is cycloalkyl or arylalkyl.

Ib $R^1$ is Cl, dimethylamino, methyl, ethyl, isopropyl, propyl, methoxy, or pyrrolidinyl; and
$R^2$ is cycloalkyl, aryl, arylakyl, or heteroaryl, which in each case is unsubstituted or substituted,
with the provisos that:
(a) when $R^1$ is methoxy, $R^2$ is cyclopentyl or pyrimidinyl substituted by dimethylamino; and
(b) when $R^1$ is pyrrolidinyl, $R^2$ is cyclopentyl or fluorine substituted benzyl.

Ic $R^1$ is Cl, dimethylamino, methyl, ethyl, isopropyl, propyl, methoxy, or pyrrolidinyl; and
$R^2$ is cyclopentyl, phenyl, benzyl or pyrimidinyl, which in each case is unsubstituted or substituted,
with the provisos that:
(a) when $R^1$ is methoxy, $R^2$ is cyclopentyl or pyrimidinyl substituted by dialkylamino; and
(b) when $R^1$ is pyrrolidinyl, $R^2$ is cyclopentyl or benzyl which is substituted or unsubstituted.

Id $R^1$ is Cl, dimethylamino, methyl, ethyl, isopropyl, propyl, methoxy, or pyrrolidinyl; and
$R^2$ is cyclopentyl, phenyl, benzyl or pyrimidinyl, which in each case is unsubstituted or substituted,
with the provisos that:
(a) when $R^1$ is methoxy, $R^2$ is cyclopentyl or pyrimidinyl substituted by dimethylamino; and
(b) when $R^1$ is pyrrolidinyl, $R^2$ is cyclopentyl or fluorine substituted benzyl.

Ie $R^1$ is Cl, dimethylamino, methyl, ethyl, isopropyl, propyl, methoxy, or pyrrolidinyl; and
$R^2$ is cyclopentyl, phenyl which is unsubstituted or substituted one or more times by alkoxy, benzyl which is unsubstituted or substituted by F, or pyrimidinyl which is unsubstituted or substituted by alkylsulfonyl, or dialkylamino,
with the provisos that:
(a) when $R^1$ is methoxy, $R^2$ is cyclopentyl or pyrimidinyl substituted by dialkylamino; and
(b) when $R^1$ is pyrrolidinyl, $R^2$ is cyclopentyl or a benzyl which is unsubstituted or substituted by F.

If $R^1$ is Cl, dimethylamino, methyl, ethyl, isopropyl, propyl, methoxy, or pyrrolidinyl; and
$R^2$ is cyclopentyl, phenyl which is unsubstituted or substituted one or more times by alkoxy, benzyl which is unsubstituted or substituted by F, or pyrimidinyl which is unsubstituted or substituted by alkylsulfonyl, or dialkylamino,
with the provisos that:
(a) when $R^1$ is methoxy, $R^2$ is cyclopentyl or pyrimidinyl substituted by dimethylamino; and
(b) when $R^1$ is pyrrolidinyl, $R^2$ is cyclopentyl or fluorine substituted benzyl.

Ig $R^1$ is Cl, dimethylamino, methyl, ethyl, isopropyl, propyl, methoxy, or pyrrolidinyl; and
$R^2$ is cyclopentyl, phenyl which is unsubstituted or substituted one or more times by methoxy, benzyl which is unsubstituted or substituted by F, or pyrimidinyl which is unsubstituted or substituted by methylsulfonyl, or dimethylamino,
with the provisos that:
(a) when $R^1$ is methoxy, $R^2$ is cyclopentyl or pyrimidinyl substituted by dialkylamino; and
(b) when $R^1$ is pyrrolidinyl, $R^2$ is cyclopentyl or a benzyl which is unsubstituted or substituted by F.

Ih $R^1$ is Cl, dimethylamino, methyl, ethyl, isopropyl, propyl, methoxy, or pyrrolidinyl; and
$R^2$ is cyclopentyl, phenyl which is unsubstituted or substituted one or more times by methoxy, benzyl which is unsubstituted or substituted by F, or pyrimidinyl which is unsubstituted or substituted by methylsulfonyl, or dimethylamino,
with the provisos that:
(a) when $R^1$ is methoxy, $R^2$ is cyclopentyl or pyrimidinyl substituted by dimethylamino; and
(b) when $R^1$ is pyrrolidinyl, $R^2$ is cyclopentyl or fluorine substituted benzyl.

Ii $R^1$ is methyl, ethyl, propyl, or cyclopropylmethyl.

Ij $R^1$ is methyl, ethyl, propyl, or cyclopropylmethyl, and $R^2$ is cycloalkyl, aryl, or heteroaryl, which in each case is unsubstituted or substituted.

In addition, preferred PDE4 inhibitors, in accordance with the invention, are compounds described by subformulas I'a-I'j, which correspond to Formula I', but exhibit the following preferred groups:

I'a R¹ is Cl, dimethylamino, methyl, ethyl, isopropyl, propyl, methoxy, or pyrrolidinyl; and
R² is cycloalkyl, aryl, arylakyl, or heteroaryl, which in each case is unsubstituted or substituted,
with the provisos that:
(a) when R¹ is methoxy, R² is cycloalkyl or pyrimidinyl substituted by dialkylamino; and
(b) when R¹ is pyrrolidinyl, R² is cycloalkyl or arylalkyl.

I'b R¹ is Cl, dimethylamino, methyl, ethyl, isopropyl, propyl, methoxy, or pyrrolidinyl; and
R² is cycloalkyl, aryl, arylakyl, or heteroaryl, which in each case is unsubstituted or substituted,
with the provisos that:
(a) when R¹ is methoxy, R² is cyclopentyl or pyrimidinyl substituted by dimethylamino; and
(b) when R¹ is pyrrolidinyl, R² is cyclopentyl or fluorine substituted benzyl.

I'c R¹ is Cl, dimethylamino, methyl, ethyl, isopropyl, propyl, methoxy, or pyrrolidinyl; and
R² is cyclopentyl, phenyl, benzyl or pyrimidinyl, which in each case is unsubstituted or substituted,
with the provisos that:
(a) when R¹ is methoxy, R² is cyclopentyl or pyrimidinyl substituted by dialkylamino; and
(b) when R¹ is pyrrolidinyl, R² is cyclopentyl or benzyl which is substituted or unsubstituted.

I'd R¹ is Cl, dimethylamino, methyl, ethyl, isopropyl, propyl, methoxy, or pyrrolidinyl; and
R² is cyclopentyl, phenyl, benzyl or pyrimidinyl, which in each case is unsubstituted or substituted,
with the provisos that:
(a) when R¹ is methoxy, R² is cyclopentyl or pyrimidinyl substituted by dimethylamino; and
(b) when R¹ is pyrrolidinyl, R² is cyclopentyl or fluorine substituted benzyl.

I'e R¹ is Cl, dimethylamino, methyl, ethyl, isopropyl, propyl, methoxy, or pyrrolidinyl; and
R² is cyclopentyl, phenyl which is unsubstituted or substituted one or more times by alkoxy, benzyl which is unsubstituted or substituted by F, or pyrimidinyl which is unsubstituted or substituted by alkylsulfonyl, or dialkylamino,
with the provisos that:
(a) when R¹ is methoxy, R² is cyclopentyl or pyrimidinyl substituted by dialkylamino; and
(b) when R¹ is pyrrolidinyl, R² is cyclopentyl or a benzyl which is unsubstituted or substituted by F.

I'f R¹ is Cl, dimethylamino, methyl, ethyl, isopropyl, propyl, methoxy, or pyrrolidinyl; and
R² is cyclopentyl, phenyl which is unsubstituted or substituted one or more times by alkoxy, benzyl which is unsubstituted or substituted by F, or pyrimidinyl which is unsubstituted or substituted by alkylsulfonyl, or dialkylamino,
with the provisos that:
(a) when R¹ is methoxy, R² is cyclopentyl or pyrimidinyl substituted by dimethylamino; and
(b) when R¹ is pyrrolidinyl, R² is cyclopentyl or fluorine substituted benzyl.

I'g R¹ is Cl, dimethylamino, methyl, ethyl, isopropyl, propyl, methoxy, or pyrrolidinyl; and
R² is cyclopentyl, phenyl which is unsubstituted or substituted one or more times by methoxy, benzyl which is unsubstituted or substituted by F, or pyrimidinyl which is unsubstituted or substituted by methylsulfonyl, or dimethylamino,
with the provisos that:
(a) when R¹ is methoxy, R² is cyclopentyl or pyrimidinyl substituted by dialkylamino; and
(b) when R¹ is pyrrolidinyl, R² is cyclopentyl or a benzyl which is unsubstituted or substituted by F.

I'h R¹ is Cl, dimethylamino, methyl, ethyl, isopropyl, propyl, methoxy, or pyrrolidinyl; and
R² is cyclopentyl, phenyl which is unsubstituted or substituted one or more times by methoxy, benzyl which is unsubstituted or substituted by F, or pyrimidinyl which is unsubstituted or substituted by methylsulfonyl, or dimethylamino,
with the provisos that:
(a) when R¹ is methoxy, R² is cyclopentyl or pyrimidinyl substituted by dimethylamino; and
(b) when R¹ is pyrrolidinyl, R² is cyclopentyl or fluorine substituted benzyl.

I'i R¹ is methyl, ethyl, propyl, or cyclopropylmethyl.

I'j R¹ is methyl, ethyl, propyl, or cyclopropylmethyl, and p2 R² is cycloalkyl, aryl, or heteroaryl, which in each case is unsubstituted or substituted.

The compounds of the present invention may be prepared conventionally. Some of the processes, which can be used, are described below. All starting materials are known or can be conventionally prepared from known starting materials.

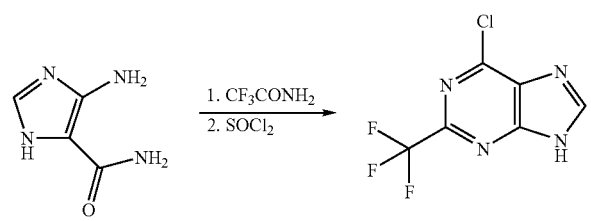

2-Substituted hypoxanthines are produced by standard methods in the art, such as by neat reaction between 4-amino-5-imidazolecarboxamide and 2,2,2-trifluoroacetamide (E. Richter et al, *J. Am. Chem. Soc.* 1960, 82, 3144-3146; or A. Giner-Sorala, et al, *J. Am. Chem. Soc.* 1958, 80, 5744-5752; or A. Parkin, et al, *J. Heterocycl. Chem.* 1982, 19, 33-40). 6-Halo-2-trifluoromethylpurine may be prepared by methods common in the art (see J.-J. Bourguignon, et al., *J. Med. Chem.* 1997, 40, 1768-1770; and H. Bader, et al., U.S. Pat. No. 4,405,781, 1983) such as by reaction with a halogenating reagent such as with $SOCl_2$, or $POCl_3$, or $PCl_5$. These reactions can be run neat or with a polar aprotic solvent such as dichloromethane, dichloroethane, or N,N-dimethylformamide.

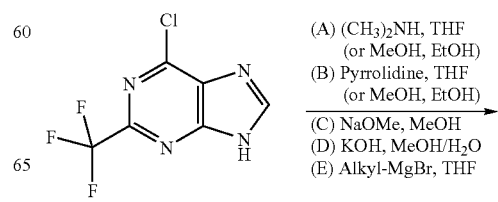

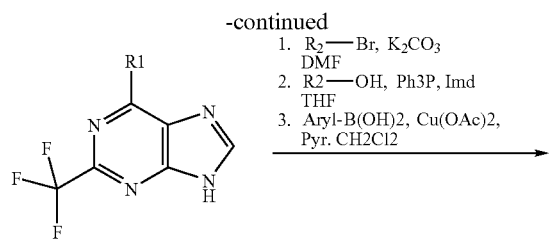

1. R$_2$—Br, K$_2$CO$_3$ DMF
2. R2—OH, Ph3P, Imd THF
3. Aryl-B(OH)2, Cu(OAc)2, Pyr. CH2Cl2

(A) R1 = (CH$_3$)N-
(B) R1 = 1-Pyrrolidine
(C) R1 = MeO-
(D) R1 = Oxo
(E) R1 = C1-C6-Alkyl
    = C4-C7-Cycloalkylalkyl
    = C3-C6-Cycloalkyl

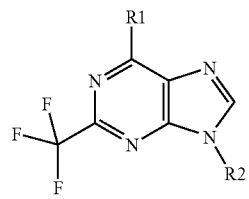

6-Dimethylamino-2-trifluoromethylpurine (A) and 6-(1-pyrrolidinyl)-2-trifluoromethylpurine (B) are prepared by standard methods in the art, such as by nucleophilic substitution reaction with 6-chloro-2-trifluormethylpurine and an appropriate secondary amine (e.g., dimethylamine or pyrrolidine) in a polar protic solvent such as MeOH or EtOH or in a polar aprotic solvent such as THF, DMF, or DMSO. 6-Methoxy-2-trifluoromethylpurine (C) is synthesized in a similar manner by reacting sodium methoxide with 6-chloro-2-trifluormethylpurine. Importantly, 6-halopurines undergo reaction with alkyl Grignard reagents (e.g., EtMgBr, THF) to produce 6-alkylpurines of general structure (E).

Subsequent alkylation reaction or N-arylation reactions provide target purine compounds of general Formula I and Formula I'. Reaction with either an alkyl halide, cycloalkyl halide, cycloalkylalkyl halide, heteroaryl halide or arylalkyl halide in a polar aprotic solvent such as N,N-dimethylformamide, dimethylsulfoxide, or dimethoxyethane, and in the presence of a base (e.g. K$_2$CO$_3$, Na$_2$CO$_3$, NaH) provides purine derivatives of Formula I and Formula I'. The use of a phase transfer catalyst, for example, 18-crown-6 or tetrabutylammonium chloride, with increased reaction temperature, e.g., 60° C. to 150° C., can be used to enhance reaction rates or reaction yields. Alternatively, reaction of 6-substituted purines under Mitsunobu conditions with an alkyl alcohol, cycloalkyl alcohol, arylalkyl alcohol, heteroarylalkyl alcohol, or cycloalkylalkyl alcohol provides 6,9-disubstituted purines of Formula I and Formula I'. In addition, 6-substituted purines undergo coupling reactions with arylboronic acids and heteroarylboronic acids in the presence of a base (e.g. triethylamine, pyridine, N-methylmorpholine), a copper catalyst (e.g., Cu(OAc)$_2$), and a polar aprotic solvent (e.g. dichloromethane, 1,4-dioxane, THF, DMF, CH$_3$CN) in a modified manner as described previously for the N-arylation of imidazole and pyrazole (see, P. Y. S. Lam et. al. Tetrahedron Lett. 1998, 39, 2941-2944) to generate 9-aryl- or 9-heteroaryl-purines of Formula I and Formula I'. Thus, preferably, the use of triethylamine, rather than pyridine, as a base, and warming to 50-60° C. in CH$_3$CN, rather than stirring at room temperature in CH$_2$Cl$_2$, provides the novel compounds. Alternatively, certain halogenated aryl and heteroaryl substrates can undergo aromatic nucleophilic substitution reaction with 6-(substituted)-2-trifluoromethylpurine in a polar aprotic solvent (e.g., DMF or DMSO) using a base (e.g., cesium carbonate) to provide target 9-aryl or 9-heteroarylpurines.

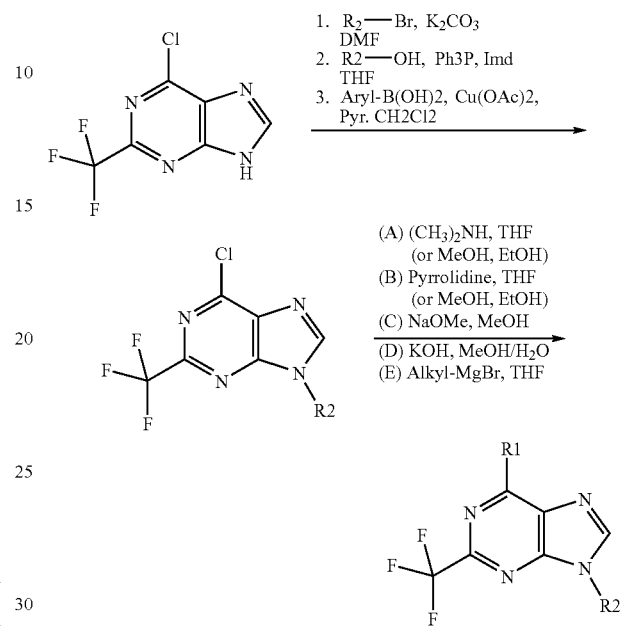

1. R$_2$—Br, K$_2$CO$_3$ DMF
2. R2—OH, Ph3P, Imd THF
3. Aryl-B(OH)2, Cu(OAc)2, Pyr. CH2Cl2

(A) (CH$_3$)$_2$NH, THF (or MeOH, EtOH)
(B) Pyrrolidine, THF (or MeOH, EtOH)
(C) NaOMe, MeOH
(D) KOH, MeOH/H$_2$O
(E) Alkyl-MgBr, THF Reaction of a 6-halopurine (e.g. 6-chloro-2-trifluoromethylpurine) with either an alkyl halide, cycloalkyl halide, cycloalkylalkyl halide, heteroaryl halide or arylalkyl halide in a polar aprotic solvent such as N,N-dimethylforamide, dimethylsulfoxide, or dimethoxyethane in the presence of a base (e.g. K$_2$CO$_3$, Na$_2$CO$_3$, NaH) provides a mixture of 9- and 7-substituted 6-halopurines.

The use of a phase transfer catalyst, for example, 18-crown-6 or tetrabutylammonium chloride, with increased reaction temperature, e.g., 60° C. to 150° C., can be used to enhance reaction rates or reaction yields. Alternatively, reaction of a 6-halopurine under Mitsunobu conditions with an alkyl alcohol, cycloalkyl alcohol, arylalkyl alcohol, heteroaryl alcohol, or cycloalkylalkyl alcohol provides a mixture of 9- and 7-substituted 6-halopurines. The 9- and 7-isomers produced by the reactions described above are readily separated by chromatography. Such 9-substituted-6-halopurines undergo reaction with alkyl Grignard reagents (e.g., EtMgBr, THF) to produce 6-alkyl-2-trifluoromethylpurines, with KOH in an aqueous alcoholic solvent to produce 6-oxo-2-trifluoromethylpurines, with secondary amines (e.g. dimethylamine or pyrrolidine) to provide purine derivatives of Formula I and Formula I', or with sodium alkoxides (e.g., NaOMe, MeOH) to produce 6-alkoxy-2-trifluoromethylpurine derivatives.

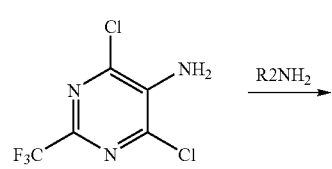

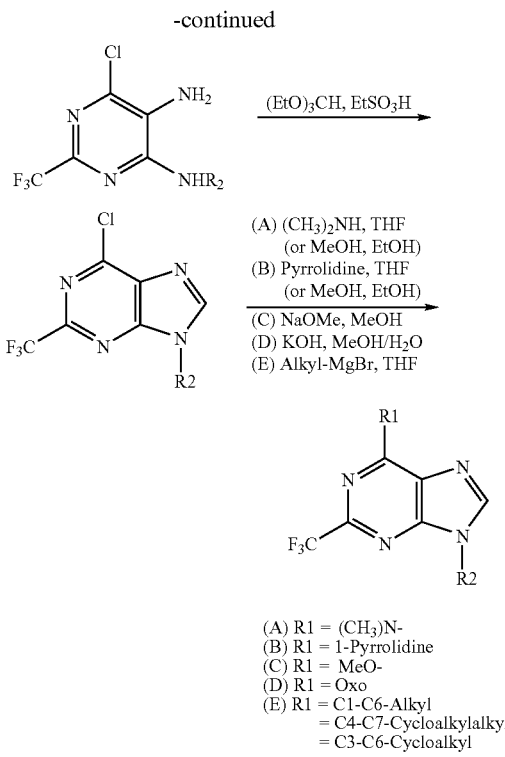
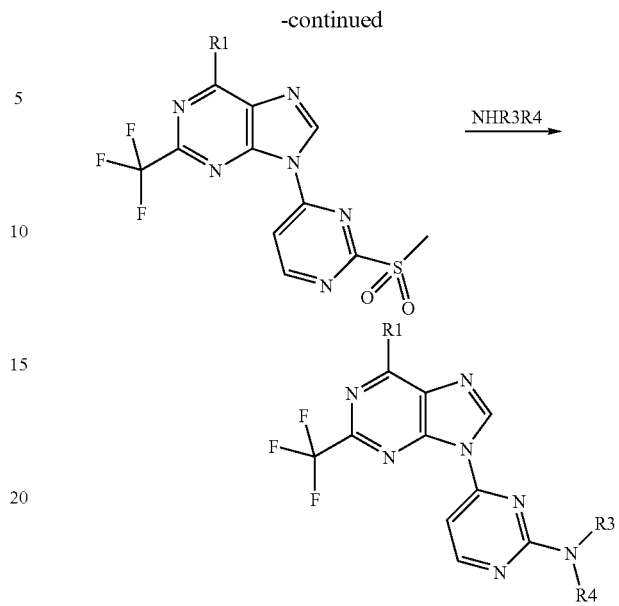

6-Substituted-9-aryl- and 9-heteroaryl-purines may be synthesized by methods common to the art, such as by reaction of a 4,6-dichloro-5-aminopyrimidine with an appropriately substituted alkylamine, cycloalkylamine, cycloalkylalkylamine, arylalkylamine, heteroarylalkylamine, aniline or heteroarylamine as described by J. L. Kelley et. al., *J. Med. Chem.*, 1997, 40, 3207 to produce 4-arylamino or 4-heteroarylamino-6-chloropyrimidines. Cyclization by treating with triethylorthoformate in the presence of an acid catalyst (e.g. ethyl sulfonic acid) provides 6-choro-9-aryl- or 9-heteroaryl-purines, which can be derivatized at the 6-position as described above to provide purine derivatives of Formula I and Formula I'.

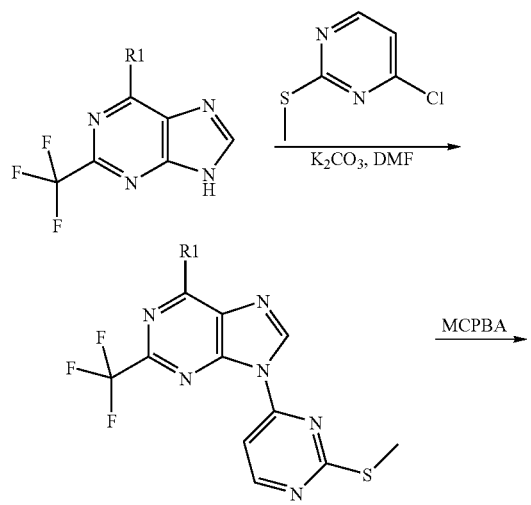

Certain halogenated aryl and heteroaryl substrates can undergo aromatic nucleophilic substitution reactions with 6-substituted-2-trifluoromethylpurines in a polar aprotic solvent (e.g., DMF or DMSO) using a base (e.g., cesium carbonate or potassium carbonate) to provide heteroarylpurines. For example, reaction of a 6-substituted-2-trifluoromethylpurine with 4-chloro-2-methylthiopyrimidine in the presence of $K_2CO_3$ in DMF provides 6-substituted-2-trifluoromethyl-9-(4-(2-methylthio)pyrimidinyl)purine. Oxidation of the methylthio moiety with a suitable oxidizing agent such as mcpba provides the methylsulfoxide derivative with one equivalent of oxidizing agent and with 2 or more equivalents, the methylsulfone is formed as depicted in the scheme above. The methylsulfone is a suitable leaving group (as would be a halogen or other sulfones) and as such undergoes nucleophilic substitution reactions with amines (e.g., methylamine, dimethylamine, morpholine, cyclopropylamine, aniline, etc.) to provide additional desired purine compounds of Formula I and Formula I'.

Many of these synthetic procedures are described more fully in the examples below.

One of ordinary skill in the art will recognize that some of the compounds of Formula I can exist in different geometrical isomeric forms. In addition, some of the compounds of the present invention possess one or more asymmetric carbon atoms and are thus capable of existing in the form of optical isomers, as well as in the form of racemic or nonracemic mixtures thereof, and in the form of diastereomers and diastereomeric mixtures inter alia. All of these compounds, including cis isomers, trans isomers, diastereomic mixtures, racemates, nonracemic mixtures of enantiomers, and substantially pure and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formula I can likewise be obtained by chiral syntheses utilizing optically active starting materials.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. No. 6,334,997.

The present invention also relates to useful forms of the compounds as disclosed herein, such as pharmaceutically acceptable salts and prodrugs of all the compounds of the present invention. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, mangnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formula I containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their high degree of PDE4 inhibition, the compounds of the present invention can be administered to anyone requiring or desiring PDE4 inhibition, and/or enhancement of cognition. Administration may be accomplished according to patient needs, for example, orally, nasally, parenterally (subcutaneously, intraveneously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for, treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below its usual dosage range.

The present invention further includes methods of treatment that involve inhibition of PDE4 enzymes. Thus, the present invention includes methods of selective inhibition of PDE4 enzymes in animals, e.g., mammals, especially humans, wherein such inhibition has a therapeutic effect, such as where such inhibition may relieve conditions involving neurological syndromes, such as the loss of memory, especially long-term memory. Such methods comprise administering to an animal in need thereof, especially a mammal, most especially a human, an inhibitory amount of a compound, alone or as part of a formulation, as disclosed herein.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Dementias are diseases that include memory loss and additional intellectual impairment separate from memory. The present invention includes methods for treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g. infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The present invention includes methods for dealing with memory loss separate from dementia, including mild cognitive impairment (MCI) and age-related cognitive decline. The present invention includes methods of treatment for memory impairment as a result of disease. In another application, the invention includes methods for dealing with memory loss resulting from the use of general anesthetics, chemotherapy, radiation treatment, post-surgical trauma, and therapeutic intervention.

The compounds may be used to treat psychiatric conditions including schizophrenia, bipolar or manic depression, major depression, and drug addiction and morphine dependence. These compounds may enhance wakefulness. PDE4 inhibitors can be used to raise cAMP levels and prevent neurons from undergoing apoptosis. PDE4 inhibitors are also known to be anti-inflammatory. The combination of anti-apoptotic and anti-inflammatory properties make these compounds useful to treat neurodegeneration resulting from any disease or injury, including stroke, spinal cord injury, neurogenesis, Alzheimer's disease, multiple sclerosis, amylolaterosclerosis (ALS), and multiple systems atrophy (MSA).

Thus, in accordance with a preferred embodiment, the present invention includes methods of treating patients suffering from memory impairment due to, for example, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions including acute neuronal diseases, as well as HIV and cardiovascular diseases, comprising administering an effective amount of a compound according to Formula I or pharmaceutically acceptable salts thereof.

The compounds of the present invention can also be used in a method of treating patients suffering from disease states characterized by decreased NMDA function, such as schizophrenia. The compounds can also be used to treat psychosis characterized by elevated levels of PDE 4, for example, various forms of depression, such as manic depression, major depression, and depression associated with psychiatric and neurological disorders.

As mentioned, the compounds of the invention also exhibit anti-inflammatory activity. As a result, the inventive compounds are useful in the treatment of a variety of allergic and inflammatory diseases, particularly disease states characterized by decreased cyclic AMP levels and/or elevated phosphodiesterase 4 levels. Thus, in accordance with a further embodiment of the invention, there is provided a method of treating allergic and inflammatory disease states, comprising administering an effective amount of a compound according to Formula I or a pharmaceutically acceptable salt thereof. Such disease states include: asthma, chronic bronchitis, chronic obstructive pulmonary disease (COPD), atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, chronic obstructive pulmonary disease, toxic and allergic contact eczema, atopic eczema, seborrheic eczema, lichen simplex, sunburn, pruritis in the anogenital area, alopecia areata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

PDE4 inhibitors for treating asthma, chronic bronchitis, psoriasis, allergic rhinitis, and other inflammatory diseases, and for inhibiting tumor necrosis factor are known within the art. See, e.g., WO 98/58901, JP11-18957, JP 10-072415, WO 93/25517, WO 94/14742, U.S. Pat. No. 5,814,651, and U.S. Pat. No. 5,935,978. These references also describe assays for determining PDE4 inhibition activity, and methods for synthesizing such compounds. The entire disclosures of these documents are hereby incorporated by reference.

PDE4 inhibitors may be used to prevent or ameliorate osteoporosis, as an antibiotic, for treatment of cardiovascular disease by mobilizing cholesterol from atherosclerotic lesions, to treat rheumatoid arthritis (RA), for long-term inhibition of mesenchymal-cell proliferation after transplantation, for treatment of urinary obstruction secondary to benign prostatic hyperplasia, for suppression of chemotaxis and reduction of invasion of colon cancer cells, for treatment of B cell chronic lymphocytic leukemia (B-CLL), for inhibition of uterine contractions, to attenuate pulmonary vascular ischemia-reperfusion injury (IRI), for corneal hydration, for inhibition of IL-2R expression and thereby abolishing HIV-1 DNA nuclear import into memory T cells, for augmentation of glucose-induced insulin secretion, in both the prevention and treatment of colitis, and to inhibit mast cell degranulation.

The compounds of the present invention can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthananine). In such combinations, each active ingredient can be administered either in accordance with their usual dosage range or a dose below their usual dosage range.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention are typically administered at dosage levels and in a mammal customary for PDE4 inhibitors such as those known compounds mentioned above. For example, the compounds can be administered, in single or multiple doses, by oral administration at a dosage level of, for example, 0.01-100 mg/kg/day, preferably 0.1-70 mg/kg/day, especially 0.5-10 mg/kg/day. Unit dosage forms can contain, for example, 0.1-50 mg of active compound. For intravenous administration, the compounds can be administered, in single or multiple dosages, at a dosage level of, for example, 0.001-50 mg/kg/day, preferably 0.001-10 mg/kg/day, especially 0.01-1 mg/kg/day. Unit dosage forms can contain, for example, 0.1-10 mg of active compound.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosure[s] of all applications, patents and publications, cited herein, and U.S. Provisional Application Ser. No. 60/401,764, filed 8 Aug. 2002, are incorporated by reference herein.

EXAMPLES

Example 1

6-(1-Propyl)-2-trifluoromethylpurine

1-Propyl magnesium bromide (3.0 mmol) was added to a mixture of 6-chloro-2-trifluoromethylpurine 222 mg (1.0 mmol), [1,3-bis(diphenylphosphino)-propane]dichloronickel(II) (0.04 mmol) and THF 15 ml at 20° C. under nitrogen. The reaction mixture was allowed to stirred at 50° C. for 12 hours, then cooled to 20 ° C., and 0.2 ml of water was added to quench the reaction. The mixture was diluted with 20 ml ethyl acetate and filtered over celite. Evaporation under vacuo and chromatography (MeOH:EtOAc:hexane=2:50:50) gave the title compound with 30% yield. $^1$H NMR (300 MHz, CDCl$_3$) δ 8.10 (s, 1H), 7.27 (t, J=8.37 Hz, 1H), 3.29 (t, J=7.5 Hz, 2H), 1.95 (m,2H), 1.02 (t, 7.5 Hz, 2H).

The following compounds were made by the same procedure
6-methyl-2-trifluoromethylpurine
6-ethyl-2-trifluoromethylpurine
6-isopropyl-2-trifluoromethylpurine
6-n-butyl-2-trifluoromethylpurine Example 2

6-N,N-dimethylamino-9-[4-(2-methylthiopyrimidinyl)]-2-trifluoromethylpurine

A mixture of 6-N,N-dimethylamino-2-trifluoromethylpurine (973 mg, 4.0 mmol), 2-methylthio-4-chloropyrimidine (866 mg, 4.8 mmol), DMF (20 ml) and potassium carbonate (1.23 g, 9 mmol) was warmed to 95° C. After 14 hours, the solvent was evaporated in vacuo. The residue was treated with 50 ml of EtOAc and washed with 5% sodium bicarbonated aqueous solution (50 ml×1). The organic layer was concentrated. Column chromatography (ethyl acetate:hexane=1:4) gave 1.04 g of the title compound (yield 69%). $^1$H NMR (300 MHz, CDCl$_3$) δ 8.99 (s, 1H), 8.70 (d, J=7.4 Hz, 1H), 8.44 (d, J=7.4 Hz), 6.12(b, 1H), 3.15 (b, 1H), 2.62 (s, 3H), 0.95 (m, 2H), 0.68 (m, 2H).

6-(1-pyrrolidinyl)-9-[4-(2-methylthiopyrimidinyl)]-2-trifluoromethylpurine was made by the same procedure.

Example 3

6-N,N-dimethylamino-9-[4-(2-methylsulfinylpyrimidinyl)]-2-trifluoromethylpurine and 6-N,N-dimethylamino-9-[4-(2-methylsulfonylpyrimidinyl)]-2-trifluoromethylpurine A mixture of 6-N,N-dimethylamino-9-[4-(2-methylthiopyrimidino)]-2-trifluoromethylpurine (183 mg, 0.5 mmol), m-chloroperoxybenzoic acid (173 mg, 1.0 mmol), dichloromethane (10 ml) was allowed to stirred at ambient temperature for 12 hours. The reaction mixture was diluted with 50 ml of ethyl acetate and filtered over celite. The filtrate was washed with 5% sodium bicarbonate aqueous solution (50 ml×3). The organic layer was concentrated and chromatographed (MeOH:EtOAc:hexane=3:50:50) to give the corresponding sulfoxide (96 mg, 50%) and sulfone (92 mg, 46%). $^1$H NMR of the sulfone (300 MHz, CDCl$_3$) δ 8.9.06 (s, 3H), 6.25(b, 1H), 3.42 (s, 3H), 3.10 (b, 1H), 0.97 (m, 2H), 0.69 (m, 2H). $^1$H NMR of sulfoxide (300 MHz, CDCl$_3$) δ 9.08 (s, 1H), 9.02 (d, J=7.2 Hz, 1H), 8.89 (d, J=7.2 Hz), 6.32(b, 1H), 3.13 (b, 1H), 3.01 (s, 3H), 0.95 (m, 2H), 0.69 (m, 2H).

The following compounds were prepared in a similar manner as described in Example 3.
a. 6-Ethyl-9-(3-methylsulfonylphenyl)-2-trifluoromethylpurine [ESMS m/z (371.3 (M+H)+)]
b. 6-Ethyl-9-(3-methylsulfinylphenyl)-2-trifluoromethylpurine [ESMS m/z (355.3 (M+H)+)]

Example 4

6-N,N-dimethylamino-9-[4-(2-dimethylaminopyrimidinyl)]-2-trifluoromethylpurine

The 6-N,N-dimethylamino-9-[4-(2-methylsulfonylpyrimidinyl)]-2-trifluoromethylpurine (38 mg, 0.1 mmol) in 10 ml of dichloromethane was treated with 1 mmol of dimethylamine for 12 hours at ambient temperature. The resulted solution was concentrated and chromatographed (EtOAc: hexane=1:3) to give 43 mg (quantitative yield) of the title compound.

The following compounds are prepared in a similar manner as described in Example 4.
6-(N,N-Dimethylamino)-9-[2-(N,N-dimethylamino)pyrimidin-4-yl]-2-trifluoromethylpurine
9-[2-(N,N-Dimethylamino)pyrimidin-4-yl]-6-methoxy-2-trifluoromethylpurine Example 5

6-Methoxy-2-trifluoromethylpurine

6-Chloro-2-trifluoromethylpurine (1.10 g, 5.0 mmol) in 25 ml of methanol was treated with 1.35 g (25 mmol) of sodium methoxide at 80° C. for 60 hours. Water (50 ml) and ethyl acetate (50 ml) were added after the reaction mixture was cooled to 20° C. The organic layer was separated and concentrated. Chromatography gave 535 mg (49%) of the title compound.

Example 6

6-Oxo-9-cyclopentyl-2-trifluoromethylpurine

6-Chloro-9-cyclopentyl-2-trifluoromethylpurine (20 mg, 0.07 mmol) was treated with 1 ml of potassium hydroxide (2 M in 90% MeOH/H$_2$O) at 70° C. for four hours. The resulting solution was cooled to 20° C. and neutralized with 3% HCl. After extraction with ethyl acetate (2×20 ml), the organic layer was combined, concentrated and chromatographed to give 19 mg (quantitative yield) of the title compound.

Example 7

6-(1-Butyl)-9-cyclopentyl-2-trifluoromethylpurine

A mixture of 6-(1-butyl)-2-trifluoromethylpurine (35 mg, 0.14 mmol), bromocyclopentane (89 mg, 0.60 mmol), potassium carbonate (83 mg, 0.6 mmol) and N,N-dimethylformamide (3 ml) was heated to 100° C. After 8 hours, the reaction mixture was cooled to 40° C. and concentrated under vacuum. The residue was treated with 15 ml of ethyl acetate and washed with 5% sodium bicarbonate (2×15 mL). The organic layer was concentrated and purified by chromatography (20% ethyl acetate in hexane) to give 6-(1-butyl)-9-cyclopentyl-2-trifluoromethylpurine (26.6 mg, 60% yield).
$^1$H NMR (300 MHz, CDCl$_3$) δ 8.20 (s, 1H), 5.04 (m, 1H), 3.24 (t, J=7.8 Hz, 2H), 2.34 (m, 2H), 1.99 (m, 4H), 1.85 (m, 4H), 1.44 (m, 2H), 0.95 (t, J=7.5 Hz, 3H). [ESMS m/z (313.4 (M+H)+)].

The following compounds were prepared in a similar fashion as described in Example 7:
a. 9-Cyclopentyl-2-trifluoromethylpurine [ESMS m/z (257.3 (M+H)+]
b. 9-Cyclopentyl-6-(1-propyl)-2-trifluoromethylpurine [ESMS m/z (299.4 (M+H)+)]
c. 9-(2,3-Difluorobenzyl)-6-ethyl-2-trifluoromethylpurine [ESMS m/z (343.0 (M+H)+]
d. 6-Ethyl-9-(3-methylbenzyl)-2-trifluoromethylpurine [ESMS m/z (321.0 (M+H)+)]
e. 6-Ethyl-9-(3-methoxybenzyl)-2-trifluoromethylpurine [ESMS m/z (337.0 (M+H)+)]
f. 9-(2,4-Difluorobenzyl)-6-ethyl-2-trifluoromethylpurine [ESMS m/z (343.0 (M+H)+)]
g. 9-Cyclopentyl-6-(N,N-dimethylamino)-2-trifluoromethylpurine
h. 6-(N,N-Dimethylamino)-9-(2-fluorobenzyl)-2-trifluoromethylpurine
i. 6-Chloro-9-(2-fluorobenzyl)-2-trifluoromethylpurine
j. 6-Chloro-9-cyclopentyl-2-trifluoromethylpurine
k. 9-Cyclopentyl-6-methoxy-2-trifluoromethylpurine
l. 9-Cyclopentyl-6-methyl-2-trifluoromethylpurine
m. 9-(2-Fluorobenzyl)-6-methyl-2-trifluoromethylpurine
n. 9-Cyclopentyl-6-ethyl-2-trifluoromethylpurine
o. 9-(2-Fluorobenzyl)-6-ethyl-2-trifluoromethylpurine
p. 9-Cyclopentyl-6-(2-propyl)-2-trifluoromethylpurine
q. 9-Cyclopentyl-6-(1-pyrrolidinyl)-2-trifluoromethylpurine
r. 9-(2-Fluorobenzyl)-6-(1-pyrrolidinyl)-2-trifluoromethylpurine Example 8

9-(3-Cyanophenyl)-6-ethyl-2-trifluoromethylpurine

A mixture of 6-ethyl-2-trifluoromethylpurine (86 mg, 0.40 mmol), 3-cyanophenylboronic acid (103 mg, 0.70 mmol), copper (II) acetate (72 mg, 0.4 mmol), triethylamine (202 mg, 2.0 mmoL), anhydrous acetonitrile (5 ml) and molecular sieves (~10 pellets) was stirred at 50-55° C. for 18 hours. Ethyl acetate (20 ml) was added and the solid was filtered off. The filtrate was washed with 20 ml of 5% aqueous sodium bicarbonate, concentrated under vacuum, and purified by chromatography over SiO$_2$ (ethyl acetate/hexane 1:3) to give 24 mg of 9-(3-cyanophenyl)-6-ethyl-2-trifluoromethylpurine (yield 19%). $^1$H NMR (300 MHz, CDCl$_3$) δ 8.50 (s, 1H), 8.11 (m, 2H), 7.82(m, 2H), 3.35 (q, J=7.5 Hz, 2H), 1.50 (t, J=7.5 Hz, 3H). [ESMS m/z (318.4 (M+H)+)]

The following compounds were prepared in a similar manner as described in Example 8.
a. 9-(2,3-Dichlorophenyl)-6-ethyl-2-trifluoromethylpurine [ESMS m/z (361.3 (M+H)+)]
b. 9-(4-Chlorophenyl)-6-ethyl-2-trifluoromethylpurine [ESMS m/z (327.4 (M+H)+)]
c. 6-Ethyl-9-(2-fluorophenyl)-2-trifluoromethylpurine [ESMS m/z (311.4 (M+H)+)]
d. 6-Ethyl-9-(3-fluorophenyl)-2-trifluoromethylpurine [ESMS m/z (311.4 (M+H)+)]
e. 9-(4-Benzyloxyphenyl)-6-ethyl-2-trifluoromethylpurine [ESMS m/z (399.5 (M+H)+)]
f. 6-Ethyl-9-(3-methylthiophenyl)-2-trifluoromethylpurine [ESMS m/z (339.5 (M+H)+)]
g. 6-Ethyl-9-(3-methylphenyl)-2-trifluoromethylpurine [ESMS m/z (307.4 (M+H)+)]
h. 6-Ethyl-9-(4-methylphenyl)-2-trifluoromethylpurine [ESMS m/z (307.1 (M+H)+)]
i. 6-Ethyl-9-(4-fluorophenyl)-2-trifluoromethylpurine [ESMS m/z (311.1 (M+H)+)]
j. 9-(2-Chlorophenyl)-6-ethyl-2-trifluoromethylpurine [ESMS m/z (327.0 (M+H)+)]
k. 6-Ethyl-9-(4-pyridyl)-2-trifluoromethylpurine [ESMS m/z (294.1 (M+H)+)]
l. 6-Ethyl-9-(4-methoxyphenyl)-2-trifluoromethylpurine [ESMS m/z (323.1 (M+H)+)]
m. 9-(3-Chlorophenyl)-6-ethyl-2-trifluoromethylpurine [ESMS m/z (327.1 (M+H)+)]
n. 9-(3-Chloro-4-pyridyl)-6-ethyl-2-trifluoromethylpurine
o. 6-Ethyl-9-(2-methyl-4-pyridyl)-2-trifluoromethylpurine
p. 6-Ethyl-9-(3-methyl-4-pyridyl)-2-trifluoromethylpurine
q. 6-Ethyl-9-(3-methoxy-4-pyridyl)-2-trifluoromethylpurine
r. 6-Ethyl-9-(3-ethylsulfonylphenyl)-2-trifluoromethylpurine [ESMS m/z (384.9 (M+H)+)]
s. 6-Ethyl-9-(3-trifluoromethoxyphenyl)-2-trifluoromethylpurine [ESMS m/z (376.9 (M+H)+)]
t. 6-Ethyl-9-(3-methoxycarbonylphenyl)-2-trifluoromethylpurine
u. 6-Ethyl-9-(4-methoxycarbonylphenyl)-2-trifluoromethylpurine
v. 6-Ethyl-9-phenyl-2-trifluoromethylpurine
w. 6-Ethyl-9-(3-methoxyphenyl)-2-trifluoromethylpurine
x. 6-Ethyl-9-(2-methoxyphenyl)-2-trifluoromethylpurine Example 9

6-Ethyl-9-(4-hydroxyphenyl)-2-trifluoromethylpurine

A mixture of 6-ethyl-9-(4-benzyloxyphenyl)-2-trifluoromethylpurine (0.1 mmol), palladium on active carbon (0.001 mol, methanol (50 mL) and acetic acid (3 mL) was shaken under 30 psi hydrogen. After 5 hours, the reaction mixture was filtered through celite and the filtrate was concentrated under vacuum. The resulting residue was dissolved in 30 mL of ethyl acetate and washed with 5% aqueous sodium bicarbonate (1×30 mL). Concentration and Chromatography (5% methanol in dichloromethane) gave 6-ethyl-9-(4-hydroxyphenyl)-2-trifluoromethylpurine (21 mg, 93%). $^1$H NMR (300 MHz, CDCl$_3$) δ 8.37 (s, 1H), 7.45 (d, J=7.2 Hz, 2H), 6.96 (d, J=7.2 Hz, 2H), 3.29 (q, J=7.5 Hz, 2 H), 3.11 (s, 1H), 1.41 (t, J=7.5 Hz, 3H). [ESMS m/z (309.4 (M+H)+)]

The following compounds were prepared in a similar manner using 9-(4-benzyloxyphenyl)-6-ethyl-2-trifluoromethylpurine or 9-(3-cyanophenyl)-6-ethyl-2-trifluoromethylpurine as starting materials:

a. 9-(3-Aminomethylphenyl)-6-ethyl-2-trifluoromethylpurine [ESMS m/z (322.4 (M+H)+)]

Example 10

9-(3-Carboxyphenyl)-6-ethyl-2-trifluoromethylpurine

6-Ethyl-9-(4-methoxycarbonylphenyl)-2-trifluoromethylpurine (500 mg, 1.43 mmol) in 10 mL of MeOH/THF/H$_2$O (1/2/1) was treated with KOH (800 mg, 14.3 mmol) and stirred for 14 hours at room temperature. The reaction mixture was concentrated under vacuum and the residue acidified to pH 4 by the addition of 30% TFA in dichloromethane and extracted with 10% MeOH in dichloromethane. The combined organic extracts were dried (Na$_2$SO$_4$), concentrated under vacuum and crystallized from MeOH to afford 9-(3-carboxyphenyl)-6-ethyl-2-trifluoromethylpurine (110 mg, 22% yield).

The following compounds were prepared in a similar fashion as described in Example 10.
a. 9-(4-Carboxyphenyl)-6-ethyl-2-trifluoromethylpurine Example 11

6-Ethyl-9-(3-methylsulfonylaminocarbonylphenyl)-2-trifluromethylpurine

A mixture of 6-ethyl-9-(3-carboxyphenyl)-2-trifluoromethylpurine (450 mg, 1.24 mmol), methylsulfonamide (238 mg, 2.48 mmol), N-ethyl-N'-3-dimethylaminopropylcarbodiimide (238 mg, 1.24 mmol), 4-dimethylaminopyridine (151 mg, 1.24 mmol) and N,N-dimethylformamide (3 ml) were stirred at 50-60° C. for 12 hours. The solvent was concentrated under vacuum, and the residue was dissolved in 30 ml of ethyl acetate, washed with sodium bicarbonate (1×30 mL), brine (1×30 mL), dried (MgSO$_4$), and concentrated. The residue was purified by chromatography over silica gel using a gradient elution from 10% to 20% MeOH/DCM to give 305 mg (56% yield) of 6-ethyl-9-(3-methylsulfonylaminocarbonylphenyl)-2-trifluromethylpurine. $^1$H NMR (300 MHz, CDCl$_3$) δ 9.43 (b, 1H), 8.59 (s, 1H), 8.30 (s, 1H), 8.18 (d, J=7.5 Hz, 1H), 7.98 (d, J=7.5 Hz, 1H), 7.78 (t, J=7.5 Hz, 1H), 3.48 (s, 3H), 3.35 (q, J=7.2 Hz, 2H), 1.52 (t, J=7.5 Hz, 3H). [ESMS m/z (414.1 (M+H)+)]

Example 12

6-(N,N-Dimethylamino)-2-trifluoromethylpurine

A mixture of 6-chloro-2-trifluoromethylpurine (45 mg, 0.20 mmol), dimethylamine (0.2 mL of a 2.0 M solution in tetrahydrofuran), triethylamine (60 mg, 0.6 mmol) and N,N-dimethylformamide (2 mL) was stirred at 85° C. for 12 hours. The solvent was removed under vacuum and the residue was dissolved in 25 mL of ethyl acetate, washed with 5% aqueous sodium bicarbonate (25 mL) and water (25 mL). The organic layer was concentrated and dried under vacuum to give crude 6-dimethylamino-2-trifluoromethylpurine (51 mg), which was used as such for the next reaction.

The following compounds were prepared in a similar manner as described in Example 12.
6-Pyrrolidin-1-yl-2-trifluoromethylpurine Additional synthesis examples of related compounds are presented in U.S. patent application Ser. No. 10/636,979 and U.S. patent application Ser. No. 10/067,996, which are incorporated herein by reference.

Example 13

In Vitro Measurement of Type 4 Phosphodiesterase Inhibition Activity

Human PDE4 was obtained from baculovirus-infected Sf9 cells that expressed the recombinant enzyme. The cDNA encoding hPDE-4D6 was subcloned into a baculovirus vector. Insect cells (Sf9) were infected with the baculovirus and cells were cultured until protein was expressed. The baculovirus-infected cells were lysed and the lysate was used as source of hPDE-4D6 enzyme. The enzyme was partially purified using a DEAE ion exchange chromatography. This procedure can be repeated using cDNA encoding other PDE-4 enzymes.

Assay

Type 4 phosphodiesterases convert cyclic adenosine monophosphate (cAMP) to 5'-adenosine monophosphate (5'-AMP). Nucleotidase converts 5'-AMP to adenosine. Therefore the combined activity of PDE4 and nucleotidase converts cAMP to adenosine. Adenosine is readily separated from cAMP by neutral alumina columns. Phosphodiesterase inhibitors block the conversion of cAMP to adenosine in this assay; consequently, PDE4 inhibitors cause a decrease in adenosine.

Cell lysates (40 ul) expressing hPDE-4D6 were combined with 50 ul of assay mix and 10 ul of inhibitors and incubated for 12 min at room temperature. Final concentrations of assay components were: 0.4 ug enzyme, 10 mM Tris-HCl (pH 7.5), 10 mM $MgCl_2$, 3 uM cAMP, 0.002 U 5'-nucleotidase, and $3 \times 10^4$ cpm of [3H]cAMP. The reaction was stopped by adding 100 µl of boiling 5 mN HCl. An aliquot of 75 µl of reaction mixture was transferred from each well to alumina columns (Multiplate; Millipore). Labeled adenosine was eluted into an OptiPlate by spinning at 2000 rpm for 2 min; 150 µl per well of scintillation fluid was added to the OptiPlate. The plate was sealed, shaken for about 30 min, and cpm of [$^3$H]adenosine was determined using a Wallac Trilux®.

All test compounds are dissolved in 100% DMSO and diluted into the assay such that the final concentration of DMSO is 0.1%. DMSO does not affect enzyme activity at this concentration.

A decrease in adenosine concentration is indicative of inhibition of PDE activity. $pIC_{50}$ values were determined by screening 6 to 12 concentrations of compound ranging from 0.1 nM to 10,000 nM and then plotting drug concentration versus $^3$H-adenosine concentration. Nonlinear regression software (Assay Explorer®) was used to estimate $pIC_{50}$ values.

Example 14

Passive Avoidance in Rats, an In Vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198-204.). The apparatus (Model E10-16SC, Coulbourn Instruments, Allentown, Pa.) consisted of a two-compartment chamber with an illuminated compartment connected to a darkened compartment by a guillotine door. The floor of the darkened compartment consisted of stainless steel rods through which an electric foot-shock could be delivered from a constant current source. All experimental groups were first habituated to the apparatus the day before the start of the experiment. During the training, the rat (Male Spraque-Dawley (Harlan) weighing 250 to 350 g) was placed in the illuminated compartment facing away from the closed guillotine door for 1 minute before the door was raised. The latency for entering the darkened compartment was recorded. After the rat entered the darkened compartment, the door was closed and a 0.5 mA electric shock was administered for 3 seconds. Twenty-four hours later, the rat was administered 0.1 mg/kg MK-801 or saline, 30 minutes prior to the injection of saline or test compound (dosed from 0.1 to 2.5 mg/kg, i.p.), which was 30 minutes before the retention test started. The rat was again placed in the illuminated compartment with the guillotine door open. The latency for entering the darkened compartment was recorded for up to 180 seconds, at which time the trial was terminated.

All data were analyzed by analyses of variance (ANOVA); individual comparisons were made using Kewman-Keuls tests. Naive rats required less than 30 seconds, on average, to cross from the illuminated compartment to the darkened compartment. However, 24 hours after the electric shock exposure, most rats pretreated with vehicle did not re-enter the darkened compartment; the average latency was increased up to 175 seconds (p<0.001). Pretreatment with MK-801 (0.1 mg/kg) markedly reduced this latency when compared to the vehicle (p<0.001). This amnesic effect of MK-801 is reversed in a statistically significant manner by actual test compounds in a dose-dependent fashion.

Example 15

Radial Arm Maze Task in Rats, an In Vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198-204.). Five days after initial housing, rats (male Spraque-Dawley (Harlan) weighing 250 to 350 g) were placed in the eight-arm radial maze (each arm was 60×10× 12 cm high; the maze was elevated 70 cm above the floor) for acclimation for two days. Rats were then placed individually in the center of the maze for 5 minutes with food pellets placed close to the food wells, and then, the next day, in the wells at the end of the arms; 2 sessions a day were conducted. Next, four randomly selected arms were then baited with one pellet of food each. The rat was restricted to the center platform (26 cm in diameter) for 15 seconds and then allowed to move freely throughout the maze until it collected all pellets of food or 10 minutes passed, whichever came first. Four parameters were recorded: 1) working memory errors, i.e., entries into baited arms that had already been visited during the same trial; 2) reference memory errors, i.e., entries into unbaited arms; 3) total arm entries; and 4) the test duration (seconds), i.e., the time spent in the collection of all the pellets in the maze. If the working memory error was zero and the average reference memory error was less than one in five successive trials, the rats began the drug tests. MK-801 or saline was injected 15 minutes prior to vehicle or test agent, which was given 45 minutes before the test. Experiments were performed in a lighted room, which contained several extra-maze visual cues.

All data were analyzed by analyses of variance (ANOVA); individual comparisons were made using Kewman-Keuls tests. Compared to control, MK-801 (0.1 mg/kg, i.p.) increased the frequencies of both working and reference memory errors (p<0.01). This amnesic effect of MK-801 on working memory is reversed in a statistically significant manner by the administration of actual test compounds in a dose-dependent fashion.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:

1. A compound of Formula I:

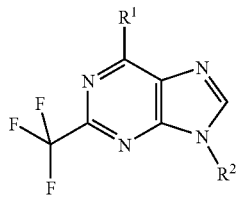

wherein, $R^1$ is alkyl having 1 to 6 carbon atoms which is unsubstituted or substituted one or more times by halogen, hydroxy, or combinations thereof, and wherein one or more —CH$_2$—CH$_2$— groups can each be replaced by —CH=CH— or —C≡C—, cycloalkyl having 3 to 6 carbon atoms, cycloallcylalkyl having 4 to 7 C atoms, methoxy, or pyrrolidinyl;

$R^2$ is alkyl having 1 to 12 carbon atoms, which is unsubstituted or substituted one or more times by halogen, hydroxy, cyano or combinations thereof, wherein one or more —CH$_2$— groups is each independently optionally replaced by —O—, —S—, or —NH—, and wherein optionally one or more —CH$_2$CH$_2$— groups is replaced in each case by —CH=CH— or —C≡C—, alkoxyalkyl having 3 to 12 carbon atoms, cycloalkyl having 3 to 12 carbon atoms, which is unsubstituted or substituted one or more times by halogen, $C_{1-4}$ alkyl, halogenated $C_{1-4}$ alkyl, $C_{1-4}$ alkylalkoxy, cyano or combinations thereof, cycloalkylalkyl having 4 to 12 C atoms, which is unsubstituted or substituted one or more times by $C_{1-4}$ alkyl, halogenated $C_{1-4}$ alkyl, $C_{1-4}$ alkyl, cyano, halogen, or combinations thereof, aryl having 6 to 14 carbon atoms which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —NR$^3$R$^4$, —CO—NH—SO$_2$—R$^5$, —SO$^2$—NH—CO—R$^5$ or combinations thereof, arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —N$^3$R$^4$, —CO—NH—SO$_2$—R$^5$, —SO$_2$—NH—CO—R$^5$ or combinations thereof, heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, morpholinyl, piperazinyl, —NR$^3$R$^4$, —CO—NH—SO$_2$R$^5$, —SO$^2$—NH—CO—R$^5$ or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, morpholinyl, piperazinyl, —NR$^3$R$^4$, —CO—NH—SO$_2$—R$^5$, —SO$^2$—NH—CO—R$^5$ or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, heterocycle-alkyl wherein the heterocycle portion has 5 to 10 ring atoms in which at least 1 ring atom is a heteroatom and the alkyl portion has 1 to 3 carbon atoms, the heterocycle portion is nonaromatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, or carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —NR$^3$R$^4$, —CO—NH—SO$_2$—R$^5$, —SO$_2$—NH—CO—R$^5$ or combinations thereof;

R$^3$ is cycloalkyl having 3 to 8 carbon atoms which is unsubstituted or substituted one or more times by halogen, C$_{1-4}$ alkyl, halogenated C$_{1-4}$ alkyl, C$_{1-4}$ alkoxy, cyano or combinations thereof, cycloalkylalkyl having 4 to 16, carbon atoms, which is unsubstituted or substituted in the cycloalkyl portion and/or the alkyl portion one or more times by halogen, oxo, cyano, hydroxy, C$_{1-4}$-alkyl, C$_{1-4}$-alkoxy, halogenated C$_{1-4}$ alkyl, halogenated C$_{1-4}$ alkoxy or combinations thereof, aryl having 6 to 14 carbon atoms which is unsubstituted or substituted one or more times by halogen, C1-4 alkyl, halogenated C1-4 alkyl, hydroxy, C$_{1-4}$-alkoxy, halogenated C$_{1-4}$ alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, —C(O)—NHOH, —C(O)—NH$_2$, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, benzyloxy, or combinations thereof, heteroaryl having 5 to 10 ring atoms in which at least 1 ring atom is a heteroatom, which is unsubstituted or substituted one or more times by halogen, aryl, C$_{1-4}$ alkyl halogenated C$_{1-4}$ alkyl, hydroxy, C$_{1-4}$-alkoxy, halogenated C$_{1-4}$ alkoxy, cyano, trifluoromethyl, nitro, amino, C$_{1-4}$-alkylamino, di-C$_{1-4}$-alkylamino, carboxy, alkoxycarbonyl, —C(O)—NHOH, —C(O)—NH$_2$, C$_{1-4}$-alkylthio, C$_{1-4}$-alkylsulphinyl, C$_{1-4}$-alkylsulphonyl, morpholinyl, piperazinyl, or combinations thereof, C$_{1-4}$-alkylsulphonyl, or C$_{1-4}$-alkyl-CO—O—C$_{1-4}$-alkylene;

R$^4$ is H or alkyl having 1 to 4 carbon atoms which is straight chain or branched, and which is unsubstituted or substituted one or more times by halogen, hydroxy, cyano or combinations thereof; and R$^5$ is alkyl having 1 to 12 carbon atoms which is unsubstituted or substituted one or more times by halogen, hydroxy, cyano or combinations thereof, wherein one or more —CH$_2$— groups is each independently optionally replaced by —O—, —S—, or NH—, and wherein optionally one or more —CH$_2$CH$_2$— groups is replaced in each case by —CH=CH— or —C≡C—, cycloalkyl having 3 to 8 carbon atoms which is unsubstituted or substituted one or more times by halogen, C$_{1-4}$ alkyl, halogenated C$_{1-4}$ alkyl, C$_{1-4}$ alkoxy, cyano or combinations thereof, cycloalkylalkyl having 4 to 16 carbon atoms, which is unsubstituted or substituted in the cycloalkyl portion and/or the alkyl portion one or more times by halogen, oxo, cyano, hydroxy, C$_{1-4}$-alkyl, C$_{1-4}$-alkoxy, halogenated C$_{1-4}$ alkyl, halogenated C$_{1-4}$ alkoxy or combinations thereof, aryl having 6 to 14 carbon atoms which is unsubstituted or substituted one or more times by halogen, C$_{1-4}$ alkyl, halogenated C$_{1-4}$ alkyl, hydroxy, C$_{1-4}$-alkoxy, halogenated C$_{1-4}$ alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, —C(O)—NHOH, —C(O)—NH$_2$, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, benzyloxy, —NR$^3$R$^4$ or combinations thereof, arylalkyl having 7 to 16 carbon atoms, which is unsubstituted or substituted one or more times by halogen, C$_{1-4}$ alkyl, halogenated C$_{1-4}$ alkyl, hydroxy, C$_{1-4}$-alkoxy, halogenated C$_{1-4}$ alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, —C(O)—NHOH, —C(O)—NH$_2$, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, benzyloxy, —NR$^3$R$^4$, or combinations thereof, heterocycle having 5 to 10 ring atoms in which at least 1 ring atom is a heteroatom, which is unsubstituted or is substituted one or more times by halogen, aryl, C$_{1-4}$ alkyl, halogenated C$_{1-4}$ alkyl, hydroxy, C$_{1-4}$-alkoxy, halogenated C$_{1-4}$ alkoxy, cyano, trifluoromethyl, nitro, oxo, amino, C$_{1-4}$-alkylamino, di-C$_{1-4}$-alkylamino, carboxy, alkoxycarbonyl, or combinations thereof, heterocycle-alkyl wherein the heterocycle portion has 5 to 10 ring atoms in which at least 1 ring atom is a heteroatom and the alkyl portion has 1 to 3 carbon atoms, the heterocycle portion is nonaromatic and is unsubstituted or is substituted one or more times by halogen, aryl, C$_{1-4}$ alkyl, halogenated C$_{1-4}$ alkyl, hydroxy, C$_{1-4}$-alkoxy, halogenated C$_{1-4}$ alkoxy, cyano, trifluoromethyl, nitro, oxo, amino, C$_{1-4}$-alkylamino, di-C$_{1-4}$-alkylamino, carboxy, alkoxycarbonyl, or combinations thereof, heteroaryl having 5 to 10 ring atoms in which at least 1 ring atom is a heteroatom which is unsubstituted or substituted one or more times by halogen, aryl, C$_{1-4}$ alkyl, halogenated C$_{1-4}$ alkyl, hydroxy, C$_{1-4}$-alkoxy, halogenated C$_{1-4}$ alkoxy, cyano, trifluoromethyl, nitro, amino, C$_{1-4}$-alkylamino, di-C$_{1-4}$-alkylamino, carboxy, alkoxycarbonyl, —C(O)—NHOH, —C(O)—NH$_2$, C$_{1-4}$-alkylthio, C$_{1-4}$-alkylsulphinyl, C$_{1-4}$-alkylsulphonyl, morpholinyl, piperazinyl, or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, C$_{1-4}$ alkyl, halogenated C$_{1-4}$ alkyl, hydroxy, C$_{1-4}$-alkoxy, halogenated C$_{1-4}$ alkoxy, cyano, trifluoromethyl, nitro, amino, C$_{1-4}$-alkylamino, di-C$_{1-4}$-alkylamino, carboxy, alkoxycarbonyl, —C(O)—NHOH, —C(O)—NH$_2$, C$_{1-4}$-alkylthio, C$_{1-4}$-alkylsulphinyl, C$_{1-4}$-alkylsulphonyl, morpholinyl, piperazinyl, —NR$^3$R$^4$, or combinations thereof;

or a pharmaceutically acceptable salt thereof, with the provisos that:

(a) when R$^1$ is methoxy, R$^2$ is cycloalkyl or pyrimidinyl substituted by dialkylamino; and (b) when R$^1$ is pyrrolidinyl, R$^2$ is cycloalkyl or arylalkyl.

2. A compound according to claim 1, wherein R$^2$ is not 4-methoxy-3-cyclopentyloxy-benzyl.

3. A compound selected from:

6-Chloro-9-(2-fluorobenzyl)-2-trifluoromethylpurine,

6-Chloro-9-cyclopentyl-2-trifluoromethylpurine,

9-Cyclopentyl-6-methoxy-2-trifluoromethylpurine, 9-(4-(2-N,N-Dimethylamino)pyrimidinyl)-6-methoxy-2-trifluoromethylpurine, 9-Cyclopentyl-6-(1-pyrrolidinyl)-2-trifluoromethylpurine, 9-(2-Fluorobenzyl)-6-(1-pyrrolidinyl)-2-trifluoromethylpurine,
9-Cyclopentyl-6-methyl-2-trifluoromethylpurine,
9-(2-Fluorobenzyl)-6-methyl-2-trifluoromethylpurine,
9-Cyclopentyl-6-ethyl-2-trifluoromethylpurine,
6-Ethyl-9-(3-fluorobenzyl)-2-trifluoromethylpurine,
6-Ethyl-9-Phenyl-2-trifluoromethylpurine,
6-Ethyl-9-(3-methoxyphenyl)-2-trifluoromethylpurine,
6-Ethyl-9-(2-methoxyphenyl)-2-trifluoromethylpurine,
9-Cyclopentyl-6-(2-propyl)-2-trifluoromethylpurine,
6-Ethyl-9-(3-methylsulfonylphenyl)-2-trifluoromethylpurine,
6-Ethyl-9-(3-methylsulfinylphenyl)-2-trifluoromethylpurine,
6-(1-Butyl)-9-cyclopentyl-2-trifluoromethylpurine,
9-Cyclopentyl-6-(1-propyl)-2-trifluoromethylpurine,
9-(2,3-Difluorobenzyl)-6-ethyl-2-trifluoromethylpurine,
6-Ethyl-9-(3-methylbenzyl)-2-trifluoromethylpurine,
6-Ethyl-9-(3-methoxybenzyl)-2-trifluoromethylpurine,
9-(2,4-Difluorobenzyl)-6-ethyl-2-trifluoromethylpurine,
9-(3-Cyanophenyl)-6-ethyl-2-trifluoromethylpurine,
9-(2,3-Dichlorophenyl)-6-ethyl-2-trifluoromethylpurine,
9-(4-Chlorophenyl)-6-ethyl-2-trifluoromethylpurine,
6-Ethyl-9-(2-fluorophenyl)-2-trifluoromethylpurine,
6-Ethyl-9-(3-fluorophenyl)-2-trifluoromethylpurine,
9-(4-Benzyloxyphenyl)-6-ethyl-2-trifluoromethylpurine,
6-Ethyl-9-(3-methylthiophenyl)-2-trifluoromethylpurine,
6-Ethyl-9-(3-methylphenyl)-2-trifluoromethylpurine,
6-Ethyl-9-(4-methylphenyl)-2-trifluoromethylpurine,
6-Ethyl-9-(4-fluorophenyl)-2-trifluoromethylpurine,
9-(2-Chlorophenyl)-6-ethyl-2-trifluoromethylpurine,
6-Ethyl-9-(4-pyridyl)-2-trifluoromethylpurine,
6-Ethyl-9-(4-methoxyphenyl)-2-trifluoromethylpurine,
9-(3-Chlorophenyl)-6-ethyl-2-trifluoromethylpurine,
9-(3-Chloro-4-pyridyl)-6-ethyl-2-trifluoromethylpurine,
6-Ethyl-9-(2-methyl-4-pyridyl)-2-trifluoromethylpurine,
6-Ethyl-9-(3-methyl-4-pyridyl)-2-trifluoromethylpurine,
6-Ethyl-9-(3-methoxy-4-pyridyl)-2-trifluoromethylpurine,
6-Ethyl-9-(3-ethylsulfonylphenyl)-2-trifluoromethylpurine,
6-Ethyl-9-(3-trifluoromethoxyphenyl)-2-trifluoromethylpurine,
6-Ethyl-9-(3-methoxycarbonylphenyl)-2-trifluoromethylpurine
6-Ethyl-9-(4-methoxycarbonylphenyl)-2-trifluoromethylpurine
6-Ethyl-9-(4-hydroxyphenyl)-2-trifluoromethylpurine,
9-(3-Aminomethylphenyl)-6-ethyl-2-trifluoromethylpurine,
9-(3-Carboxyphenyl)-6-ethyl-2-trifluoromethylpurine,
9-(4-Carboxyphenyl)-6-ethyl-2-trifluoromethylpurine,
6-Ethyl-9-(3-methylsulfonylaminocarbonylphenyl)-2-trifluoromethylpurine; and
pharmaceutically acceptable salts thereof.

4. A compound according to claim 1, wherein $R^2$ is aryl substituted by —CO—NH—SO$_2$—$R^5$.

5. A compound according to claim 1, wherein $R^2$ is phenyl substituted by —CO—NH—SO$_2$—$R^5$.

6. A compound according to claim 4, wherein $R^5$ is alkyl.

7. A compound according to claim 5, wherein $R^5$ is alkyl.

8. A compound according to claim 1, wherein $R^2$ is aryl substituted by —SO$_2$—NH—CO—$R^5$.

9. A compound according to claim 1, wherein $R^2$ is phenyl substituted by —SO$_2$—NH—CO—$R^5$.

10. A compound according to claim 8, wherein $R^5$ is alkyl.

11. A compound according to claim 9, wherein $R^5$ is alkyl.

12. A compound of Formula I:

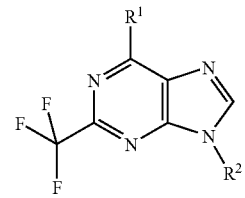

wherein, $R^1$ is alkyl having 1 to 6 carbon atoms which is unsubstituted or substituted one or more times by halogen, hydroxy, or combinations thereof and wherein one or more —CH$_2$—CH$_2$— groups can each be replaced by —CH=CH— or —C≡C—,
cycloalkyl having 3 to 6 carbon atoms,
cycloalkylalkyl having 4 to 7 C atoms,
methoxy, or
pyrrolidinyl;

$R^2$ is alkyl 1 to 12 carbon atoms, which is unsubstituted or substituted one or more times by halogen, hydroxy, cyano or combinations thereof, wherein one or more —CH$_2$— groups is each independently optionally replaced by —O—, —S—, or —NH—, and wherein optionally one or more —CH$_2$CH$_2$— groups is replaced in each case by —CH=CH— or —C≡C—,
alkoxyalkyl having 3 to 12 carbon atoms,
cycloalkyl having 3 to 12 carbon atoms, which is unsubstituted or substituted one or more times by halogen, C$_{1-4}$ alkyl, halogenated C$_{1-4}$ alkyl, C$_{1-4}$ alkoxy, cyano or combinations thereof,
cycloalkylalkyl having 4 to 12 C atoms, which is unsubstituted or substituted one or more times by C$_{1-4}$ alkyl, halogenated C$_{1-4}$ alkyl, C$_{1-4}$ alkoxy, cyano, halogen, or combinations thereof,
aryl having 6 to 14 carbon atoms which is unsubstituted or substituted one or more times by halogen, C$_{1-4}$ alkyl, halogenated C$_{1-4}$ alkyl, hydroxy, C$_{1-4}$-alkoxy, halogenated C$_{1-4}$ alkoxy, nitro, methylenedioxy, ethylenedioxy, amino, C$_{1-4}$alkylamino, di-C$_{1-4}$-alkylamino, C$_{1-4}$-hydroxyalkyl, C$_{1-4}$-hydroxyalkoxy, carboxy, cyano, —C(O)—NHOH, —C(O)—NH$_2$, C$_{2-4}$-acyl, C$_{2-4}$-alkoxycarbonyl, C$_{1-4}$alkylthio, C$_{1-4}$-alkylsulphinyl, C$_{1-4}$-alkylsulphonyl, phenoxy, benzyloxy, —NR$^3$R$^4$ or combinations thereof,
arylalkyl having 7 to 16 carbon atoms, which is unsubstituted or substituted one or more times by halogen, C$_{1-4}$ alkyl, halogenated C$_{1-4}$ alkyl, hydroxy, C$_{1-4}$-alkoxy, halogenated C$_{1-4}$ alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, —C(O)—NHOH, —C(O)—NH$_2$, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof,
heteroaryl having 5 to 10 ring atoms in which at least 1 ring atom is a heteroatom, which is unsubstituted or substituted one or more times by halogen, aryl, C$_{1-4}$ alkyl, halogenated C$_{1-4}$ alkyl, hydroxy, C$_{1-4}$-alkoxy, halogenated C$_{1-4}$ alkoxy, cyano, trifluoromethyl, nitro, amino, C$_{1-4}$-alkylamino, di-C$_{1-4}$-alkylamino, carboxy, alkoxycarbonyl, —C(O)—NHOH, —C(O)—NH$_2$, C$_{1-4}$-alkylthio, C$_{1-4}$-alkylsulphinyl, $C_{1-4}$-alkylsulphonyl, morpholinyl, piperazinyl, —NR$^3$R$^4$ or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof heterocycle-alkyl wherein the heterocycle portion has 5 to 10 ring atoms in which at least 1 ring atom is a heteroatom and the alkyl portion has 1 to 3 carbon atoms, the heterocycle portion is nonaromatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, or carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, or combinations thereof;

R$^3$ is cycloalkyl having 3 to 8 carbon atoms which is unsubstituted or substituted one or more times by halogen, $C_{1-4}$ alkyl, halogenated $C_{1-4}$ alkyl, $C_{1-4}$ alkoxy, cyano or combinations thereof, aryl having 6 to 14 carbon atoms which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, or combinations thereof, heteroaryl having 5 to 10 ring atoms in which at least 1 ring atom is a heteroatom which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, morpholinyl, piperazinyl, or combinations thereof, $C_{1-4}$-alkylsulphonyl, or
$C_{1-4}$-alkyl-CO—O—$C_{1-4}$-alkylene; and R$^4$ is H or alkyl having 1 to 4 carbon atoms which is straight chain or branched; or a pharmaceutically acceptable salt thereof,
with the provisos that:
(a) when R$^1$ is methoxy, R$^2$ is cycloalkyl or pyrimidinyl substituted by dialkylamino; and
(b) when R$^1$ is pyrrolidinyl, R$^2$ is cycloalkyl or arylalkyl.

13. A compound according to claim 12, wherein R$^2$ is not 4-methoxy-3-cyclopentyloxy-benzyl.

14. A compound selected from:
6-Chloro-9-(2-fluorobenzyl)-2-trifluoromethylpurine,
6-Chloro-9-cyclopentyl-2-trifluoromethylpurine,
9-Cyclopentyl-6-methoxy-2-trifluoromethylpurine,
9-(4-(2-N,N-Dimethylamino)pyrimidinyl)-6-methoxy-2-trifluoromethylpurine,
9-Cyclopentyl-6-(1-pyrrolidinyl)-2-trifluoromethylpurine,
9-(2-Fluorobenzyl)-6-(1-pyrrolidinyl)-2-trifluoromethylpurine,
9Cyclopentyl-6-methyl-2-trifluoromethylpurine,
9-(2-Fluorobenzyl)-6-methyl-2-trifluoromethylpurine,
9Cyclopentyl-6-ethyl-2-trifluoromethylpurine,
9-(2-Fluorobenzyl)-6-ethyl-2-trifluoromethylpurine,
9-Phenyl-6-ethyl-2-trifluoromethylpurine,
6-Ethyl-9-(3-methoxyphenyl)-2-trifluoromethylpurine,
6-Ethyl-9-(2-methoxyphenyl)-2-trifluoromethylpurine,
9-Cyclopentyl-6-(2-propyl)-2-trifluoromethylpurine, and pharmaceutically acceptable salts thereof.

15. A compound according to claim 12, wherein R$^1$ is an alkyl having up to 5 carbon atoms.

16. A compound according to claim 12, wherein R$^1$ is an alkyl having 1 to 4 carbon atoms.

17. A compound according to claim 12, wherein R$^1$ is an alkyl having 1 to 3 carbon atoms.

18. A compound according to claim 12, wherein R$^1$ is methyl, ethyl, propyl, isopropyl, butyl, isopropyl, pentyl, 1-methylbutyl, 2-methylbutyl, 3-methylbutyl, 1,1-dimethylpropyl, 2,2-dimethylpropyl or 1-ethylpropyl.

19. A compound according to claim 12, wherein R$^2$ is methyl, ethyl, propyl, isopropyl, butyl, isopropyl, pentyl, 1-methylbutyl, 2-methylbutyl, 3-methylbutyl, 1,1-dimethylpropyl, 2,2-dimethylpropyl, 1-ethylpropyl, hexyl, heptyl, octyl, nonyl, decyl, undecyl, dodecyl, 1-, 2-, 3- or 4-methylpentyl, tert-butyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, or dimethylbutyl.

20. A compound according to claim 12, wherein R$^2$ is an alkyl having 3 to 8 carbon atoms.

21. A compound according to claim 12, wherein R$^2$ is an alkyl having 3 to 6 carbon atoms.

22. A compound according to claim 12, wherein heteroaryl is an aromatic heterocyclic group having one or two rings containing 1 to 3 hetero-ring atoms selected from N, O and S, which is unsubstituted or substituted in one or more places by halogen, hydroxyl, aryl, alkyl, alkoxy, carboxy, methylene, cyano, trifluoromethyl, nitro, amino, alkylamino, dialkylamino, or combinations thereof.

23. A compound according to claim 12, wherein heteroaryl is an aromatic heterocyclic group selected from furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, thiadiazolyl, pyridyl, pyridazinyl, pyrimidinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl, which in each case is unsubstituted or substituted in one or more places by halogen, hydroxyl, aryl, alkyl, alkoxy, carboxy, cyano, trifluoromethyl, nitro, amino, alkylamino, dialkylamino, or combinations thereof.

24. A compound according to claim 12, wherein heteroaryl is an aromatic heterocyclic group selected from 2-thienyl, 3-thienyl, 2-, 3- or 4-pyridyl, 2-, 3-, 4-, 5-, 6-, 7- or 8-quinolinyl, and 1-, 3-, 4-, 5-, 6-, 7-, or 8-isoquinolinyl, which in each case is unsubstituted or substituted in one or more places by halogen, hydroxyl, aryl, alkyl, alkoxy, carboxy, cyano, trifluoromethyl, nitro, amino, alkylamino, dialkylamino, or combinations thereof.

25. A compound according to claim 12, wherein heteroarylalkyl is pyridylmethyl, thienylmethyl, pyrimidinylmethyl, pyrazinylmethyl, or isoquinolinylmethyl, wherein heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, or combinations thereof.

26. A compound according to claim 12, wherein heteroarylalkyl is pyridylmethyl, thienylmethyl, pyrimidinylmethyl, pyrazinylmethyl, or isoquinolinylmethyl.

27. A compound according to claim 12, wherein heterocycle is a non-aromatic cyclic group containing at least one hetero-ring atom selected from N, S and O.

28. A compound according to claim 12, wherein heterocycle is 3-tetrahydrofuranyl, piperidinyl, imidazolinyl, imidazolidinyl, pyrrolinyl, pyrrolidinyl, morpholinyl, piperazinyl, or indolinyl.

29. A compound according to claim 12, wherein heterocycle-alkyl is piperidinyl-ethyl and pyrrolinyl-methyl.

30. A compound according to claim 12, wherein carbocycle is a non-aromatic monocyclic or bicyclic structures containing 6 to 10 carbon atoms.

31. A compound according to claim 12, wherein carbocycle is cyclopentenyl, cyclohexenyl, cyclohexadienyl, tetrahydronaphthenyl or indan-2-yl.

32. A compound according to claim 12, wherein $R^1$ is methoxy, pyrrolidinyl, methyl, ethyl or isopropyl.

33. A compound according to claim 12, wherein $R^2$ is cycloalkyl, aryl, arylalkyl, or heteroaryl.

34. A compound according to claim 12, wherein $R^2$ is cyclopentyl, phenyl, benzyl, or pyrimidinyl.

35. A compound according to claim 12, wherein $R^2$ is cyclopentyl, phenyl which is unsubstituted or substituted, benzyl which is unsubstituted or substituted, or pyrimidinyl which is unsubstituted or substituted.

36. A compound according to claim 12, wherein $R^2$ is cyclopentyl, phenyl which is unsubstituted or substituted one or more times by, alkoxy, benzyl which is unsubstituted or substituted by F, or pyrimidinyl which is unsubstituted or substituted by alkylsulfonyl or dialkylamino.

37. A compound according to claim 12, wherein:
$R^1$ is methyl, ethyl, isopropyl, propyl, methoxy, or pyrrolidinyl; and
$R^2$ is cycloalkyl, aryl, arylalkyl, or heteroaryl, which in each case is unsubstituted or substituted,
with the provisos that:
(a) when $R^1$ is methoxy, $R^2$ is cycloalkyl or pyrimidinyl substituted by dialkylamino; and
(b) when $R^1$ is pyrrolidinyl, $R^2$ is cycloalkyl or arylalkyl.

38. A compound according to claim 12, wherein:
$R^1$ is methyl, ethyl, isopropyl, propyl, methoxy, or pyrrolidinyl; and
$R^2$ is cycloalkyl, aryl, arylalkyl, or heteroaryl, which in each case is unsubstituted or substituted,
with the provisos that:
(a) when $R^1$ is methoxy, $R^2$ is cyclopentyl or pyrimidinyl substituted by dimethylamino; and
(b) when $R^1$ is pyrrolidinyl, $R^2$ is cyclopentyl or fluorine substituted benzyl.

39. A compound according to claim 12, wherein:
$R^1$ is methyl, ethyl, isopropyl, propyl, methoxy, or pyrrolidinyl; and
$R^2$ is cyclopentyl, phenyl, benzyl or pyrimidinyl, which in each case is unsubstituted or substituted,
with the provisos that:
(a) when $R^1$ is methoxy, $R^2$ is cyclopentyl or pyrimidinyl substituted by dialkylamino; and
(b) when $R^1$ is pyrrolidinyl, $R^2$ is cyclopentyl or benzyl which is substituted or unsubstituted.

40. A compound according to claim 12, wherein:
$R^1$ is methyl, ethyl, isopropyl, propyl, methoxy, or pyrrolidinyl; and
$R^2$ is cyclopentyl, phenyl, benzyl or pyrimidinyl, which in each case is unsubstituted or substituted,
with the provisos that:
(a) when $R^1$ is methoxy, $R^2$ is cyclopentyl or pyrimidinyl substituted by dimethylamino; and
(b) when $R^1$ is pyrrolidinyl, $R^2$ is cyclopentyl or fluorine substituted benzyl.

41. A compound according to claim 12, wherein:
$R^1$ is methyl, ethyl, isopropyl, propyl, methoxy, or pyrrolidinyl; and
$R^2$ is cyclopentyl, phenyl which is unsubstituted or substituted one or more times by alkoxy, benzyl which is unsubstituted or substituted by F, or pyrimidinyl which is unsubstituted or substituted by alkylsulfonyl, or dialkylamino,
with the provisos that:
(a) when $R^1$ is methoxy, $R^2$ is cyclopentyl or pyrimidinyl substituted by dialkylamino; and
(b) when $R^1$ is pyrrolidinyl, $R^2$ is cyclopentyl or a benzyl which is unsubstituted or substituted by F.

42. A compound according to claim 12, wherein:
$R^1$ is methyl, ethyl, isopropyl, propyl, methoxy, or pyrrolidinyl; and
$R^2$ is cyclopentyl, phenyl which is unsubstituted or substituted one or more times by alkoxy, benzyl which is unsubstituted or substituted by F, or pyrimidinyl which is unsubstituted or substituted by alkylsulfonyl, or dialkylamino,
with the provisos that:
(a) when $R^1$ is methoxy, $R^2$ is cyclopentyl or pyrimidinyl substituted by dimethylamino; and
(b) when $R^1$ is pyrrolidinyl, $R^2$ is cyclopentyl or fluorine substituted benzyl.

43. A compound according to claim 12, wherein:
$R^1$ is methyl, ethyl, isopropyl, propyl, methoxy, or pyrrolidinyl; and
$R^2$ is cyclopentyl, phenyl which is unsubstituted or substituted one or more times by methoxy, benzyl which is unsubstituted or substituted by F, or pyrimidinyl which is unsubstituted or substituted by methylsulfonyl, or dimethylamino,
with the provisos that:
(a) when $R^1$ is methoxy, $R^2$ is cyclopentyl or pyrimidinyl substituted by dialkylamino; and (b) when R¹ is pyrrolidinyl, R² is cyclopentyl or a benzyl which is unsubstituted or substituted by F.

44. A compound according to claim 12, wherein:
R¹ is methyl, ethyl, isopropyl, propyl, methoxy, or pyrrolidinyl; and
R² is cyclopentyl, phenyl which is unsubstituted or substituted one or more times by methoxy, benzyl which is unsubstituted or substituted by F, or pyrimidinyl which is unsubstituted or substituted by methylsulfonyl, or dimethylamino,
with the provisos that:
(a) when R¹ is methoxy, R² is cyclopentyl or pyrimidinyl substituted by dimethylamino; and
(b) when R¹ is pyrrolidinyl, R² is cyclopentyl or fluorine substituted benzyl.

45. A compound according to claim 12, wherein R¹ is methyl, ethyl, propyl, or cyclopropylmethyl.

46. A compound according to claim 12, wherein R¹ is methyl, ethyl, propyl, or cyclopropylmethyl, and R² is cycloalkyl, aryl, or heteroaryl, which in each case is unsubstituted or substituted.

47. A pharmaceutical composition containing a compound of claim 1 and a pharmaceutically acceptable carrier.

48. A composition of claim 47, wherein the compound of claim 1 is provided in a unit dosage of 0.1-50 mg.

49. A pharmaceutical composition containing a compound of claim 12 and a pharmaceutically acceptable carrier.

50. A composition of claim 49, wherein the compound of claim 12 is provided in a unit dosage of 0.1-50 mg.

51. A compound of Formula I:

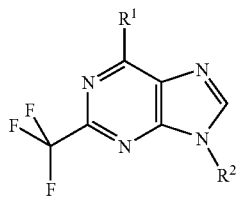

I wherein,
R¹ is halogen,
dimethylamino,
alkyl having 1 to 6 carbon atoms which is unsubstituted or substituted one or more times by halogen, hydroxy, or combinations thereof, and wherein a —CH₂— group can be optionally replaced by —O—, —S—, or —NCH—, and/or one or more —CH₂—CH₂— groups can each be replaced by —CH═CH— or —C≡C—,
cycloalkyl having 3 to 6 carbon atoms,
cycloalkylalkyl having 4 to 7 C atoms,
methoxy, or
pyrrolidinyl;
R² is aryl having 6 to 14 carbon atoms which is substituted one or more times by —CO—NH—SO₂—R⁵ or —SO₂—NH—CO—R⁵;
R³ is cycloalkyl having 3 to 8 carbon atoms which is unsubstituted or substituted one or more times by halogen, $C_{1-4}$ alkyl, halogenated $C_{1-4}$ alkyl, $C_{1-4}$ alkoxy, cyano or combinations thereof,
cycloalkylalkyl having 4 to 16 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy, halogenated $C_{1-4}$ alkyl, halogenated $C_{1-4}$ alkoxy or combinations thereof,
aryl having 6 to 14 carbon atoms which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH₂, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, or combinations thereof,
heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH₂, $C_{1-4}$-alkylthio, $C_{1-4}$-alkylsulphinyl, $C_{1-4}$-alkylsulphonyl, morpholinyl, piperazinyl, or combinations thereof,
$C_{1-1}$-alkylsulphonyl, or
$C_{1-1}$-alkyl-CO—O—$C_{1-4}$-alkylene;
R⁴ is H or alkyl having 1 to 4 carbon atoms which is straight chain or branched, and which is unsubstituted or substituted one or more times by halogen, hydroxy, cyano or combinations thereof; and
R⁵ is alkyl having 1 to 12 carbon atoms which is unsubstituted or substituted one or more times by halogen, hydroxy, cyano or combinations thereof, wherein one or more —CH₂— groups is each independently optionally replaced by —O—, —S—, or NH—, and wherein optionally one or more —CH₂CH₂— groups is replaced in each case by —CH═CH— or —C≡C—,
cycloalkyl having 3 to 8 carbon atoms which is unsubstituted or substituted one or more times by halogen, $C_{1-4}$ alkyl, halogenated $C_{1-4}$ alkyl, $C_{1-4}$ alkoxy, cyano or combinations thereof,
cycloalkylalkyl having 4 to 16, which is unsubstituted or substituted in the cycloalkyl portion and/or the alkyl portion one or more times by halogen, oxo, cyano, hydroxy, $C_{1-4}$-alkyl, $C_{1-4}$-alkoxy, halogenated $C_{1-4}$ alkyl, halogenated $C_{1-4}$ alkoxy or combinations thereof,
aryl having 6 to 14 carbon atoms which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH₂, C2-4-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —NR³R⁴ or combinations thereof,
arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH₂, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, benzyloxy, —NR³R⁴, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, heterocycle-alkyl wherein the heterocycle portion has 5 to 10 ring atoms in which at least 1 ring atom is a heteroatom and the alkyl portion has 1 to 3 carbon atoms, the heterocycle portion is nonaromatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, heteroaryl having 5 to 10 ring atoms in which at least 1 ring atom is a heteroatom which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, morpholinyl, piperazinyl, or combinations thereof, or heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, morpholinyl, piperazinyl, —NR$^3$R$^4$, or combinations thereof; and pharmaceutically acceptable salts thereof.

52. A pharmaceutical composition containing a compound of claim 3 and a pharmaceutically acceptable carrier.

53. A pharmaceutical composition containing a compound of claim 14 and a pharmaceutically acceptable carrier.

54. A pharmaceutical composition containing a compound of claim 51 and a pharmaceutically acceptable carrier.

55. A compound according to claim 3, wherein said compound is 9-cyclopentyl-6-ethyl-2-trifluoromethylpurine, or a pharmaceutically acceptable salt thereof.

56. A compound according to claim 55, wherein said compound is 9-cyclopentyl-6-ethyl-2-trifluoromethylpurine.

57. A pharmaceutical composition containing a compound of claim 55 and a pharmaceutically acceptable carrier.

58. A pharmaceutical composition containing a compound of claim 56 and a pharmaceutically acceptable carrier.

59. A compound according to claim 3, wherein said compound is 9-(4-carboxyphenyl)-6-ethyl-2-trifluoromethylpurine, or a pharmaceutically acceptable salt thereof.

60. A compound according to claim 59, wherein said compound is 9-(4-carboxyphenyl)-6-ethyl-2-trifluoromethylpurine.

61. A pharmaceutical composition containing a compound of claim 59 and a pharmaceutically acceptable carrier.

62. A pharmaceutical composition containing a compound of claim 60 and a pharmaceutically acceptable carrier.

* * * * *

UNITED STATES PATENT AND TRADEMARK OFFICE
CERTIFICATE OF CORRECTION

PATENT NO. : 7,335,654 B2 Page 1 of 1
APPLICATION NO. : 10/636996
DATED : February 26, 2008
INVENTOR(S) : Allen T. Hopper It is certified that error appears in the above-identified patent and that said Letters Patent is hereby corrected as shown below:

Column 42, line 1 reads "–$SO^{2}$", should read -- –$SO_2$--
Column 42, line 24 reads "–$SO^{2}$", should read -- –$SO_2$--
Column 42, line 37 reads "–$SO^{2}$", should read -- –$SO_2$--
Column 45, line 6 reads "-9-(3-", should read -- -9-(2- --
Column 51, line 50 reads "–NCH-", should read -- –$NCH_3$- --
Column 52, line 54 reads "C2-4", should read --$C_{2-4}$--

Signed and Sealed this

Second Day of December, 2008

JON W. DUDAS
*Director of the United States Patent and Trademark Office*